United States Patent [19]

Zhu et al.

[11] Patent Number: 5,695,939
[45] Date of Patent: Dec. 9, 1997

[54] PLANT DEFENSE GENES AND PLANT DEFENSE REGULATORY ELEMENTS

[75] Inventors: Qun Zhu; Christopher J. Lamb, both of San Diego, Calif.

[73] Assignee: The Salk Institute for Biological Studies, La Jolla, Calif.

[21] Appl. No.: 379,259

[22] Filed: Jan. 27, 1995

Related U.S. Application Data

[62] Division of Ser. No. 704,288, May 22, 1991, Pat. No. 5,399,680.
[51] Int. Cl.$^6$ .......................... C12N 15/11; C12N 15/56; C12Q 1/68
[52] U.S. Cl. .......................... 435/6; 536/23.2; 536/24.3
[58] Field of Search ..................... 536/23.2, 24.3; 435/6

[56] References Cited

FOREIGN PATENT DOCUMENTS

WO8912059  12/1989  WIPO.

OTHER PUBLICATIONS

Kim et al., Biosci. Biotech. Biochem. 58:1164–1166 (1994).
Nishizawa et al., Mol. Gen. Genet. 241:1–10 (1993).
Kuhn et al., Induction of phenylalanine ammonia–lyase and 4–coumarate:CoA ligase mRNAs in cultured plant cells by UV light or fungal elicitor, Proceedings of the National Academy of Science USA vol. 81:1102–1106 (1984).

Ryder et al., Elicitor rapidly induces chalcone synthase mRNA in *Phaseolus vulgaris* cells at the onset of the phytoalexin defense response, Proceedings of the National Academy of Science USA vol. 81:5724–5728 (1984).

Jones, Phenylalanine Ammonia–lyase: Regulation of its Induction and its Role in Plant Development, Phytochemistry 23:1349–1359 (1984).

Kaulen et al., Light–induced expression of the chimeric chalcone synthase–NPTII gene in tobacco cells, EMBO Journal vol. 5:1–8 (1980).

Hahlbrock et al., Rapid Response of Suspension–cultured Parsley Cells to the Elicitor from *Phytophthora megasperma* var. *sojae*, Plant Physiology vol. 67:768–773 (1981).

Darnell, Variety in the level of gene control in eukaryotic cells, Nature vol. 297:365–371 (1982).

*Primary Examiner*—Eric Grimes
*Attorney, Agent, or Firm*—Stephen E. Reiter; Gray, Cary, Ware & Freidenrich

[57] ABSTRACT

Novel chitinase gene, and its associated regulatory region, from a monocotyledon plant is described.

7 Claims, 7 Drawing Sheets

```
            10                  30                  50
RICE     MRALAVVAMVARPF.....LAAAVHAEQCGSQAGGAVCPNCLCCSQFGWCGSTSDYCGAG
TOBACCO  ............SL     LLSAS         R ASG      K     N N     P
POTATO1  ....TIFSLLFSLL     LN SGSN...VVHRPD L APG    K     N N     P
POTATO2  RHKE NF YLLFSLLV   VS AL QN      G KA ASGQ   K     N N     S
BEAN     IWSVG  W L...L     VGGSYG       R    L GGN              T P 70                  90                 110
RICE     CQSQCSRLRRRRPDASGGGGSGVASIVSRSLFDLMLLHRNDAACPA.SNFYTYDAFVAA
TOBACCO  N       P......GGPTPP   GDLG  I S M  Q  K    N  QG KG  S N   IN
POTATO1  N       P........GGP PSGDLGGVI N M  Q  N    N  QGKN    S N   IS
POTATO2  N       P.....GGGPGP P GDLG AI N M  Q  K    ENS QG K   S N   IN
BEAN             ........GGPSPAPTDLSALI    T  Q  K    G    KG          I 130                 150                 170
RICE     ASAFPGFAAAGDADTNKREVAAFLAQTSHETTGGWATAPDGPYTWGYCFKEENGGAGPDY
TOBACCO   RS     GTS   TTAR  I  F                    A   WLR Q SP .
POTATO1   GS     GTT   ITAR  I                  PS   A   LR  Q SP .
POTATO2   RS     GTS   INAR  I  F                S   A   LR  R NP .
BEAN      K Y S  GNT   TA R  I   G                   A   VR  RNPST..

190                 210                 230
RICE     CQQSAQWPCAAGKKYYGRGPIQLSYNFNYGPAGQAIGADLLGDPDLVASDATVSFDTAFW
TOBACCO  TP G    P R F      I H Y    C R  V    NN    T  PVI   KS L
POTATO1  TP S    P R F      I H Y    C R  V    NN    T  SVI   KS I
POTATO2  PP S    P R F      I H Y    C R AV    NN    T  PVI   K  L
BEAN     SATP F  P QQ       I W Y   QC R  V    NK    T  SVI   KS L 250                 270                 290
RICE     FWMTPQSPKPSCNAVATGQWTPSADDQRAGRVPGYGVITNIINGGLECGHGEDDRIADRI
TOBACCO          HD II R Q   SA RA N L   F           R T S   VQ
POTATO1          HD I  R Q   GA    N     F                S S VQ
POTATO2          HD II R N   SA RA N L   F           R T N   VQ
BEAN         A   SHD I  SR   SA VA R L    TV                R Q S VQ 310                 330
RICE     GFYKRYCDILGVSYGANLDCYSQRPSAPP....KLRLPSFHTVINNH*
TOBACCO    R    S    P D    GN  SFGNGLLVDTM*
POTATO1    R    G    P D    GN  SFGNG   L .....VD  *
POTATO2    R    S    TP D   VN  WFGNALL  ..VDTL*
BEAN       F       L   G  N     T FGNS    L . SDLV SQ*
```

|  | HEVEIN DOMAIN | SPACER | CATALYTIC DOMAIN |
|---|---|---|---|
|  | EQCGRQAGGKLCPNNLCCSQWGWCGSTDEYCSPDHNCQSNCKD | | |
| HEVEIN | Q......K A......SG......FG......P F......SQG | R TG | |
| WIN1 | Q......R A......G......FG......S P......SQG | O TG | |
| WIN2 | -K S S..................GS......LGS F......-GGG | GACS | |
| WGA | | | |
| RICE | S......AV......C......FG......SD......GAG-- | Q | SRIRRRPDASGGGGSGVASIVSRSLFDLMLL |
| BEAN | ......A......GGN......FG......TD......G G-- | Q | --GGPSPAP----TDLSALI-SRSTFDQMLK |
| BASIC | S......AR......SG......KFG......N ND......G G- | Q | PGGPTPTPPTPPGGGDLGSII-SSSMFDQMLK |
| PR-Q | | | QGIGS-IVTSDLFNEMLK |
| PR-P | | | QGIGS-IVTNDLFNEMLK |

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
( A ) LENGTH: 1884 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:1:

| | | | | | | |
|---|---|---|---|---|---|---|
| GTTAACTGCC | AGCTTCAAAT | TATTTATAGA | TAATTTAATA | GCCAATTCAT | CTAATAGTTA | 60 |
| TTTATTATAC | TATTAATATC | TGATCTCACC | TGAGTCATAC | TACAGCTGGC | TACAAATGTG | 120 |
| TAGTGTACTA | CTCTTTCTCT | CTTCTTTTAT | CTCTTTAAAA | TATGTTATAG | CGGCTTATAA | 180 |
| CTGTTATTGT | ACCTGCTCTA | AGTCGATCGT | GATGATCGAT | CATTCGTCAA | ATGTTACCAC | 240 |
| GTCCAGTGAC | TTATCCATGG | TTCACCTTAC | TATAAAAAAT | GATTTTATG | GACAACTCCT | 300 |
| TTAATTTGT | TCAAACGGAC | CAAAGAAACC | CGTATGTAAA | AAGGTTGGGA | ATATCTGATC | 360 |
| CTGTATGTAA | AAAGCTTGGA | ATATCTGATA | GAGGGCAAAC | TTGTGAAAAT | TGTTTTTTA | 420 |
| AGATGGACCT | CTTAACAAGC | CTACTTGCAA | AAAATCGACC | TATTTACATA | GACGGACTTG | 480 |
| TTAAGAGACT | TGTCTATGAA | AATCGGTGGA | TAGCATGACC | GGTCACAATA | CTTCCCCTAT | 540 |
| AATTTTTAA | TCCTCCTAGA | TAAACCCTAT | CTCTCTCTTC | ATGTTCTTTG | CTTTCCATCT | 600 |
| ATAGTCTCGC | ATCCCTCATC | ACCTCCCATT | CCTCTCTCTC | TCACCCCCTG | CTCAGTGGGA | 660 |
| GCGCAGCTGG | CGATGGCACC | ACCGGCGACA | AGAGGGGCCA | GAGGCTAGCA | TGTGCACGGA | 720 |
| AGTGACAATG | GCGCCACATG | ATTAGCATGG | GAGCAGCGGC | GCGTTTCATC | AGGACACGCT | 780 |
| GCAATTGGCT | CTAGTGACGG | CACCCTTGAG | AGGACATGGT | AGCGGTGGCG | CCTCAGGAGT | 840 |
| GGTGGGGCAC | GGTGGCAGAA | CTCCGGCGGT | GGCAAGCCAC | CACACAGCGA | CAGATCCACC | 900 |
| ACCACCGACC | TTGGGAGCAG | CGGGGCCTCA | GCGGTGATGA | CGATGGTAGA | TCGAAGCTAG | 960 |
| GGTTTCTATT | TTTTTTTGCT | GCAAAAATCA | CTTTTTACAC | ATGGGTACAT | GCATGTTTTT | 1020 |
| TACATACACC | TAGTATTAGG | TGGGCCGTCC | ACCCGTTCGC | AAAGATCATT | TATGCAGTCA | 1080 |
| TCATGATCGG | AGATGGAACT | ATGGAGACAT | ATATGCAAGT | ATTTGGCCAA | CATGTCCAAT | 1140 |
| GTCCACCAGA | TTGGGAGCTC | AATCCTACCC | CGTGGTATGG | GTATGTTACT | GTGCGCCTAA | 1200 |
| TATTTACGTA | CGCTGGTTTA | ATCTATTTTT | AAAAAATTTG | CTACATACTC | CCTCCGTCCC | 1260 |
| CAAGGTTGGC | TTTTTTTTTT | TGGAGGGAGA | GAGTAATATT | TAGAGTTTGT | GGTTTTTGTT | 1320 |
| ATTGAACACC | TTAAAAGGCA | TGAAACGACT | TGTCGGAGAA | CGAATCTCCT | CTAGCAGGGA | 1380 |
| AGCAACGAAC | CTCCCAAAAA | AAACAAAAAA | AAACTCCTCC | TTTCATGATT | CAACCAAAGG | 1440 |
| GCAATTTGAG | ATCGAGCCTA | CTCTGTGTGA | TGAACTCAAA | ACACAATCAA | GTATACTTGT | 1500 |
| GTGATGAGCG | GTGAGCCAGA | TATGTTCCTG | CTCTGTCCGT | GCTCGACTCA | ATTCATTGTC | 1560 |
| AACCCTAGCG | ATTTCCATTA | ATGCAATGAC | TATATGAAAT | GCAAAGATGT | ACTATATGAC | 1620 |
| TACTAGTTGG | ATGCACAATA | GTGCTACTAT | GGAACCCCTT | TTGCCCCTCT | AATAGTAGGA | 1680 |
| TCTAGGCTAA | ATGACGTTTC | AATAAATCAC | AGTTAGTAAG | GGATGCATGC | ATATGCATGA | 1740 |
| TATGTGAGTG | TCTGTTAATC | GTGGCAAATT | GGCAATGCAA | TTTGTTGTTG | AAAAATACCA | 1800 |

```
AGATGCCAAT ACTACGCCCA CTTCCCGCGG CGCTCTATAT AAAGCCATGC GCTCCCATCG   1860

CTTCTTCCTC ACAAACTTTC CCTC                                          1884
```

( 2 ) INFORMATION FOR SEQ ID NO:2:

( i ) SEQUENCE CHARACTERISTICS:
        ( A ) LENGTH: 1151 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 55..1062

( x i ) SEQUENCE DESCRIPTION: SEQ ID NO:2:

```
AATCAGTCAA TCTGTATACA GCAACTCAGC GATCTTATAT TTACCCAACA CACC ATG       57
                                                            Met
                                                            1

AGA GCG CTC GCT GTG GTG GCC ATG GTG GCC AGG CCC TTC CTC GCG GCG      105
Arg Ala Leu Ala Val Val Ala Met Val Ala Arg Pro Phe Leu Ala Ala
        5                  10                 15

GCC GTG CAT GCC GAG CAG TGC GGC AGC CAG GCC GGC GGC GCG GTG TGC      153
Ala Val His Ala Glu Gln Cys Gly Ser Gln Ala Gly Gly Ala Val Cys
         20                 25                 30

CCC AAC TGC CTC TGC TGC AGC CAG TTC GGC TGG TGC GGC TCC ACC TCC      201
Pro Asn Cys Leu Cys Cys Ser Gln Phe Gly Trp Cys Gly Ser Thr Ser
         35                 40                 45

GAC TAC TGC GGC GCC GGA TGC CAG AGC CAG TGC TCG CGG CTG CGG CGG      249
Asp Tyr Cys Gly Ala Gly Cys Gln Ser Gln Cys Ser Arg Leu Arg Arg
 50                 55                 60                 65

CGG CGG CCC GAC GCG TCC GGC GGC GGT GGC AGC GGC GTC GCG TCC ATC      297
Arg Arg Pro Asp Ala Ser Gly Gly Gly Ser Gly Val Ala Ser Ile
                 70                 75                 80

GTG TCG CGC TCG CTC TTC GAC CTG ATG CTG CTC CAC CGC AAC GAT GCG      345
Val Ser Arg Ser Leu Phe Asp Leu Met Leu Leu His Arg Asn Asp Ala
             85                 90                 95

GCG TGC CCG GCC AGC AAC TTC TAC ACC TAC GAC GCC TTC GTC GCC GCC      393
Ala Cys Pro Ala Ser Asn Phe Tyr Thr Tyr Asp Ala Phe Val Ala Ala
        100                105                110

GCC AGC GCC TTC CCG GGC TTC GCC GCC GCG GGC GAC GCC GAC ACC AAC      441
Ala Ser Ala Phe Pro Gly Phe Ala Ala Ala Gly Asp Ala Asp Thr Asn
        115                120                125

AAG CGC GAG GTC GCC GCG TTC CTT GCG CAG ACG TCC CAC GAG ACC ACC      489
Lys Arg Glu Val Ala Ala Phe Leu Ala Gln Thr Ser His Glu Thr Thr
130                135                140                145

GGC GGG TGG GCG ACG GCG CCC GAC GGC CCC TAC ACG TGG GGC TAC TGC      537
Gly Gly Trp Ala Thr Ala Pro Asp Gly Pro Tyr Thr Trp Gly Tyr Cys
                150                155                160

TTC AAG GAG GAG AAC GGC GGC GCC GGG CCG GAC TAC TGC CAG CAG AGC      585
Phe Lys Glu Glu Asn Gly Gly Ala Gly Pro Asp Tyr Cys Gln Gln Ser
            165                170                175

GCG CAG TGG CCG TGC GCC GCC GGC AAG AAG TAC TAC GGC CGG GGT CCC      633
Ala Gln Trp Pro Cys Ala Ala Gly Lys Lys Tyr Tyr Gly Arg Gly Pro
        180                185                190

ATC CAG CTC TCC TAC AAC TTC AAC TAC GGG CCG GCG GGG CAG GCC ATC      681
Ile Gln Leu Ser Tyr Asn Phe Asn Tyr Gly Pro Ala Gly Gln Ala Ile
        195                200                205

GGC GCC GAC CTG CTC GGC GAC CCG GAC CTC GTG GCG TCT GAC GCC ACC      729
Gly Ala Asp Leu Leu Gly Asp Pro Asp Leu Val Ala Ser Asp Ala Thr
210                215                220                225
```

```
GTC  TCC  TTC  GAC  ACG  GCC  TTC  TGG  TTC  TGG  ATG  ACG  CCG  CAG  TCG  CCC    777
Val  Ser  Phe  Asp  Thr  Ala  Phe  Trp  Phe  Trp  Met  Thr  Pro  Gln  Ser  Pro
               230                      235                     240

AAG  CCG  TCG  TGC  AAC  GCG  GTC  GCC  ACC  GGC  CAG  TGG  ACG  CCC  TCC  GCC    825
Lys  Pro  Ser  Cys  Asn  Ala  Val  Ala  Thr  Gly  Gln  Trp  Thr  Pro  Ser  Ala
               245                      250                     255

GAC  GAC  CAG  CGG  GCG  GGC  CGC  GTG  CCG  GGC  TAC  GGC  GTC  ATC  ACC  AAC    873
Asp  Asp  Gln  Arg  Ala  Gly  Arg  Val  Pro  Gly  Tyr  Gly  Val  Ile  Thr  Asn
               260                      265                     270

ATC  ATC  AAC  GGC  GGG  CTG  GAG  TGC  GGC  CAT  GGC  GAG  GAC  GAT  CGC  ATC    921
Ile  Ile  Asn  Gly  Gly  Leu  Glu  Cys  Gly  His  Gly  Glu  Asp  Asp  Arg  Ile
               275                      280                     285

GCC  GAC  CGG  ATC  GGC  TTC  TAC  AAG  CGC  TAC  TGC  GAC  ATC  CTC  GGC  GTC    969
Ala  Asp  Arg  Ile  Gly  Phe  Tyr  Lys  Arg  Tyr  Cys  Asp  Ile  Leu  Gly  Val
290                      295                      300                     305

AGC  TAC  GGC  GCC  AAC  TTG  GAT  TGC  TAC  AGC  CAG  AGG  CCT  TCG  GCT  CCT   1017
Ser  Tyr  Gly  Ala  Asn  Leu  Asp  Cys  Tyr  Ser  Gln  Arg  Pro  Ser  Ala  Pro
               310                      315                     320

CCT  AAG  CTT  CGC  CTA  CCT  AGC  TTC  CAC  ACA  GTG  ATA  AAT  AAT  CAC        1062
Pro  Lys  Leu  Arg  Leu  Pro  Ser  Phe  His  Thr  Val  Ile  Asn  Asn  His
               325                      330                     335

TGATGGAGTA TAGTTTACAC CATATCGATG AATAAAACTT GATCCGAATT CTCGCCCTAT                 1122

AGTGAGTCGT ATTAGTCGAC AGCTCTAGA                                                  1151
```

( 2 ) INFORMATION FOR SEQ ID NO:3:

( i ) SEQUENCE CHARACTERISTICS:
    ( A ) LENGTH: 336 amino acids
    ( B ) TYPE: amino acid
    ( D ) TOPOLOGY: linear ( i i ) MOLECULE TYPE: protein ( x i ) SEQUENCE DESCRIPTION: SEQ ID NO:3:

```
Met  Arg  Ala  Leu  Ala  Val  Val  Ala  Met  Val  Ala  Arg  Pro  Phe  Leu  Ala
 1              5                        10                      15

Ala  Ala  Val  His  Ala  Glu  Gln  Cys  Gly  Ser  Gln  Ala  Gly  Gly  Ala  Val
               20                       25                      30

Cys  Pro  Asn  Cys  Leu  Cys  Cys  Ser  Gln  Phe  Gly  Trp  Cys  Gly  Ser  Thr
               35                       40                      45

Ser  Asp  Tyr  Cys  Gly  Ala  Gly  Cys  Gln  Ser  Gln  Cys  Ser  Arg  Leu  Arg
          50                       55                      60

Arg  Arg  Arg  Pro  Asp  Ala  Ser  Gly  Gly  Gly  Ser  Gly  Val  Ala  Ser
 65                       70                      75                      80

Ile  Val  Ser  Arg  Ser  Leu  Phe  Asp  Leu  Met  Leu  Leu  His  Arg  Asn  Asp
               85                       90                      95

Ala  Ala  Cys  Pro  Ala  Ser  Asn  Phe  Tyr  Thr  Tyr  Asp  Ala  Phe  Val  Ala
              100                      105                     110

Ala  Ala  Ser  Ala  Phe  Pro  Gly  Phe  Ala  Ala  Ala  Gly  Asp  Ala  Asp  Thr
              115                      120                     125

Asn  Lys  Arg  Glu  Val  Ala  Ala  Phe  Leu  Ala  Gln  Thr  Ser  His  Glu  Thr
          130                      135                     140

Thr  Gly  Gly  Trp  Ala  Thr  Ala  Pro  Asp  Gly  Pro  Tyr  Thr  Trp  Gly  Tyr
145                      150                      155                     160

Cys  Phe  Lys  Glu  Glu  Asn  Gly  Gly  Ala  Gly  Pro  Asp  Tyr  Cys  Gln  Gln
                        165                      170                     175

Ser  Ala  Gln  Trp  Pro  Cys  Ala  Ala  Gly  Lys  Lys  Tyr  Tyr  Gly  Arg  Gly
              180                      185                     190
```

| Pro | Ile | Gln | Leu | Ser | Tyr | Asn | Phe | Asn | Tyr | Gly | Pro | Ala | Gly | Gln | Ala |
|---|---|---|---|---|---|---|---|---|---|---|---|---|---|---|---|
| | | 195 | | | | | 200 | | | | | 205 | | | |

| Ile | Gly | Ala | Asp | Leu | Leu | Gly | Asp | Pro | Asp | Leu | Val | Ala | Ser | Asp | Ala |
|---|---|---|---|---|---|---|---|---|---|---|---|---|---|---|---|
| 210 | | | | | 215 | | | | | 220 | | | | | |

| Thr | Val | Ser | Phe | Asp | Thr | Ala | Phe | Trp | Phe | Trp | Met | Thr | Pro | Gln | Ser |
|---|---|---|---|---|---|---|---|---|---|---|---|---|---|---|---|
| 225 | | | | | 230 | | | | | 235 | | | | | 240 |

| Pro | Lys | Pro | Ser | Cys | Asn | Ala | Val | Ala | Thr | Gly | Gln | Trp | Thr | Pro | Ser |
|---|---|---|---|---|---|---|---|---|---|---|---|---|---|---|---|
| | | | | 245 | | | | | 250 | | | | | 255 | |

| Ala | Asp | Asp | Gln | Arg | Ala | Gly | Arg | Val | Pro | Gly | Tyr | Gly | Val | Ile | Thr |
|---|---|---|---|---|---|---|---|---|---|---|---|---|---|---|---|
| | | | 260 | | | | | 265 | | | | | 270 | | |

| Asn | Ile | Ile | Asn | Gly | Gly | Leu | Glu | Cys | Gly | His | Gly | Glu | Asp | Asp | Arg |
|---|---|---|---|---|---|---|---|---|---|---|---|---|---|---|---|
| | | 275 | | | | | 280 | | | | | 285 | | | |

| Ile | Ala | Asp | Arg | Ile | Gly | Phe | Tyr | Lys | Arg | Tyr | Cys | Asp | Ile | Leu | Gly |
|---|---|---|---|---|---|---|---|---|---|---|---|---|---|---|---|
| | 290 | | | | | 295 | | | | | 300 | | | | |

| Val | Ser | Tyr | Gly | Ala | Asn | Leu | Asp | Cys | Tyr | Ser | Gln | Arg | Pro | Ser | Ala |
|---|---|---|---|---|---|---|---|---|---|---|---|---|---|---|---|
| 305 | | | | | 310 | | | | | 315 | | | | | 320 |

| Pro | Pro | Lys | Leu | Arg | Leu | Pro | Ser | Phe | His | Thr | Val | Ile | Asn | Asn | His |
|---|---|---|---|---|---|---|---|---|---|---|---|---|---|---|---|
| | | | | 325 | | | | | 330 | | | | | 335 | |

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:4:

CCGAACTGGC TGCAGAGGCA GTTGG                      25

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:5:

CCCTCAATCT                                      10

( 2 ) INFORMATION FOR SEQ ID NO:6:

( i ) SEQUENCE CHARACTERISTICS:
        ( A ) LENGTH: 310 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:6:

| Met | Ser | Leu | Leu | Leu | Leu | Ser | Ala | Ser | Ala | Glu | Gln | Cys | Gly | Ser | Gln |
|---|---|---|---|---|---|---|---|---|---|---|---|---|---|---|---|
| 1 | | | | 5 | | | | | 10 | | | | | 15 | |

| Ala | Gly | Gly | Ala | Arg | Cys | Ala | Ser | Gly | Leu | Cys | Cys | Ser | Lys | Phe | Gly |
|---|---|---|---|---|---|---|---|---|---|---|---|---|---|---|---|
| | | | 20 | | | | | 25 | | | | | 30 | | |

| Trp | Cys | Gly | Asn | Thr | Asn | Asp | Tyr | Cys | Gly | Pro | Gly | Asn | Cys | Gln | Ser |
|---|---|---|---|---|---|---|---|---|---|---|---|---|---|---|---|
| | | 35 | | | | | 40 | | | | | 45 | | | |

```
Gln Cys Pro Gly Gly Pro Thr Pro Pro Gly Gly Gly Asp Leu Gly Ser
    50                  55                  60

Ile Ile Ser Ser Ser Met Phe Asp Gln Met Leu Lys His Arg Asn Asp
65                  70                  75                  80

Asn Ala Cys Gln Gly Lys Gly Phe Tyr Ser Tyr Asn Ala Phe Ile Asn
                85                  90                  95

Ala Ala Arg Ser Phe Pro Gly Phe Gly Thr Ser Gly Asp Thr Thr Ala
            100                 105                 110

Arg Lys Arg Glu Ile Ala Ala Phe Phe Ala Gln Thr Ser His Glu Thr
        115                 120                 125

Thr Gly Gly Trp Ala Thr Ala Pro Asp Gly Pro Tyr Ala Trp Gly Tyr
    130                 135                 140

Cys Trp Leu Arg Glu Gln Gly Ser Pro Gly Asp Tyr Cys Thr Pro Ser
145                 150                 155                 160

Gly Gln Trp Pro Cys Ala Pro Gly Arg Lys Tyr Phe Gly Arg Gly Pro
                165                 170                 175

Ile Gln Ile Ser His Asn Tyr Asn Tyr Gly Pro Cys Gly Arg Ala Ile
            180                 185                 190

Gly Val Asp Leu Leu Asn Asn Pro Asp Leu Val Ala Thr Asp Pro Val
        195                 200                 205

Ile Ser Phe Lys Ser Ala Leu Trp Phe Trp Met Thr Pro Gln Ser Pro
    210                 215                 220

Lys Pro Ser Cys His Asp Val Ile Ile Gly Arg Trp Pro Ser Ser Ala
225                 230                 235                 240

Asp Arg Ala Ala Asn Arg Leu Pro Gly Phe Gly Val Ile Thr Asn Ile
                245                 250                 255

Ile Asn Gly Gly Leu Glu Cys Gly Arg Gly Thr Asp Ser Arg Val Gln
            260                 265                 270

Asp Arg Ile Gly Phe Tyr Arg Arg Tyr Cys Ser Ile Leu Gly Val Ser
        275                 280                 285

Pro Gly Asp Asn Leu Asp Cys Gly Asn Gln Arg Ser Phe Gly Asn Gly
    290                 295                 300

Leu Leu Val Asp Thr Met
305                 310
```

(2) INFORMATION FOR SEQ ID NO:7:

(i) SEQUENCE CHARACTERISTICS:
        (A) LENGTH: 314 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:7:

```
Thr Ile Phe Ser Leu Leu Phe Ser Leu Leu Leu Asn Ala Ser Gly
1               5                   10                  15

Ser Asn Val Val His Arg Pro Asp Ala Leu Cys Ala Pro Gly Leu Cys
                20                  25                  30

Cys Ser Lys Phe Gly Trp Cys Gly Asn Thr Asn Asp Tyr Cys Gly Pro
            35                  40                  45

Gly Asn Cys Gln Ser Gln Cys Pro Gly Gly Pro Gly Pro Ser Gly Asp
        50                  55                  60

Leu Gly Gly Val Ile Ser Asn Ser Met Phe Asp Gln Met Leu Asn His
65                  70                  75                  80

Arg Asn Asp Asn Ala Cys Gln Gly Lys Asn Asn Phe Tyr Ser Tyr Asn
```

|   |   |   |   |   | 85 |   |   |   |   | 90 |   |   |   |   | 95 |   |
|---|---|---|---|---|---|---|---|---|---|---|---|---|---|---|---|---|
| Ala | Phe | Ile | Ser | Ala | Ala | Gly | Ser | Phe | Pro | Gly | Phe | Gly | Thr | Thr | Gly |
|  |  |  | 100 |  |  |  |  | 105 |  |  |  | 110 |  |  |  |

| Asp | Ile | Thr | Ala | Arg | Lys | Arg | Glu | Ile | Ala | Ala | Phe | Leu | Ala | Gln | Thr |
|---|---|---|---|---|---|---|---|---|---|---|---|---|---|---|---|
|  |  | 115 |  |  |  | 120 |  |  |  |  | 125 |  |  |  |  |

| Ser | His | Glu | Thr | Thr | Gly | Gly | Trp | Pro | Ser | Ala | Pro | Asp | Gly | Pro | Tyr |
|---|---|---|---|---|---|---|---|---|---|---|---|---|---|---|---|
|  | 130 |  |  |  |  | 135 |  |  |  | 140 |  |  |  |  |  |

| Ala | Trp | Gly | Tyr | Cys | Phe | Leu | Arg | Glu | Gln | Gly | Ser | Pro | Gly | Asp | Tyr |
|---|---|---|---|---|---|---|---|---|---|---|---|---|---|---|---|
| 145 |  |  |  |  | 150 |  |  |  | 155 |  |  |  |  |  | 160 |

| Cys | Thr | Pro | Ser | Ser | Gln | Trp | Pro | Cys | Ala | Pro | Gly | Arg | Lys | Tyr | Phe |
|---|---|---|---|---|---|---|---|---|---|---|---|---|---|---|---|
|  |  |  |  | 165 |  |  |  | 170 |  |  |  |  | 175 |  |  |

| Gly | Arg | Gly | Pro | Ile | Gln | Ile | Ser | His | Asn | Tyr | Asn | Tyr | Gly | Pro | Cys |
|---|---|---|---|---|---|---|---|---|---|---|---|---|---|---|---|
|  |  |  | 180 |  |  |  |  | 185 |  |  |  | 190 |  |  |  |

| Gly | Arg | Ala | Ile | Gly | Val | Asp | Leu | Leu | Asn | Asn | Pro | Asp | Leu | Val | Ala |
|---|---|---|---|---|---|---|---|---|---|---|---|---|---|---|---|
|  |  | 195 |  |  |  | 200 |  |  |  |  | 205 |  |  |  |  |

| Thr | Asp | Ser | Val | Ile | Ser | Phe | Lys | Ser | Ala | Ile | Trp | Phe | Trp | Met | Thr |
|---|---|---|---|---|---|---|---|---|---|---|---|---|---|---|---|
|  | 210 |  |  |  |  | 215 |  |  |  |  | 220 |  |  |  |  |

| Pro | Gln | Ser | Pro | Lys | Pro | Ser | Cys | His | Asp | Val | Ile | Thr | Gly | Arg | Trp |
|---|---|---|---|---|---|---|---|---|---|---|---|---|---|---|---|
| 225 |  |  |  |  | 230 |  |  |  | 235 |  |  |  |  |  | 240 |

| Pro | Ser | Gly | Ala | Asp | Gln | Ala | Ala | Asn | Arg | Val | Pro | Gly | Phe | Gly | Val |
|---|---|---|---|---|---|---|---|---|---|---|---|---|---|---|---|
|  |  |  |  | 245 |  |  |  |  | 250 |  |  |  |  | 255 |  |

| Ile | Thr | Asn | Ile | Ile | Asn | Gly | Gly | Leu | Glu | Cys | Gly | His | Gly | Ser | Asp |
|---|---|---|---|---|---|---|---|---|---|---|---|---|---|---|---|
|  |  |  | 260 |  |  |  |  | 265 |  |  |  |  | 270 |  |  |

| Ser | Arg | Val | Gln | Asp | Arg | Ile | Gly | Phe | Tyr | Arg | Arg | Tyr | Cys | Gly | Ile |
|---|---|---|---|---|---|---|---|---|---|---|---|---|---|---|---|
|  |  | 275 |  |  |  |  | 280 |  |  |  |  | 285 |  |  |  |

| Leu | Gly | Val | Ser | Pro | Gly | Asp | Asn | Leu | Asp | Cys | Gly | Asn | Gln | Arg | Ser |
|---|---|---|---|---|---|---|---|---|---|---|---|---|---|---|---|
|  | 290 |  |  |  |  | 295 |  |  |  |  | 300 |  |  |  |  |

| Phe | Gly | Asn | Gly | Leu | Leu | Val | Asp | Thr | Val |
|---|---|---|---|---|---|---|---|---|---|
| 305 |  |  |  |  | 310 |  |  |  |  |

(2) INFORMATION FOR SEQ ID NO:8:

(i) SEQUENCE CHARACTERISTICS:
 (A) LENGTH: 330 amino acids
 (B) TYPE: amino acid
 (C) STRANDEDNESS: unknown
 (D) TOPOLOGY: unknown (ii) MOLECULE TYPE: protein (xi) SEQUENCE DESCRIPTION: SEQ ID NO:8:

| Met | Arg | Arg | His | Lys | Glu | Val | Asn | Phe | Val | Ala | Tyr | Leu | Leu | Phe | Ser |
|---|---|---|---|---|---|---|---|---|---|---|---|---|---|---|---|
| 1 |  |  |  | 5 |  |  |  |  | 10 |  |  |  |  | 15 |  |

| Leu | Leu | Val | Leu | Val | Ser | Ala | Ala | Leu | Ala | Gln | Asn | Cys | Gly | Ser | Gln |
|---|---|---|---|---|---|---|---|---|---|---|---|---|---|---|---|
|  |  |  | 20 |  |  |  |  | 25 |  |  |  | 30 |  |  |  |

| Gly | Gly | Gly | Lys | Ala | Cys | Ala | Ser | Gly | Gln | Cys | Cys | Ser | Lys | Phe | Gly |
|---|---|---|---|---|---|---|---|---|---|---|---|---|---|---|---|
|  |  | 35 |  |  |  | 40 |  |  |  |  | 45 |  |  |  |  |

| Trp | Cys | Gly | Asn | Thr | Asn | Asp | Tyr | Cys | Gly | Ser | Gly | Asn | Cys | Gln | Ser |
|---|---|---|---|---|---|---|---|---|---|---|---|---|---|---|---|
|  | 50 |  |  |  | 55 |  |  |  | 60 |  |  |  |  |  |  |

| Gln | Cys | Pro | Gly | Gly | Gly | Pro | Gly | Pro | Gly | Pro | Gly | Gly | Asp | Leu | Gly |
|---|---|---|---|---|---|---|---|---|---|---|---|---|---|---|---|
| 65 |  |  |  |  | 70 |  |  |  | 75 |  |  |  |  |  | 80 |

| Ser | Ala | Ile | Ser | Asn | Ser | Met | Phe | Asp | Gln | Met | Leu | Lys | His | Arg | Asn |
|---|---|---|---|---|---|---|---|---|---|---|---|---|---|---|---|
|  |  |  |  | 85 |  |  |  |  | 90 |  |  |  |  | 95 |  |

| Glu | Asn | Ser | Cys | Gln | Gly | Lys | Asn | Phe | Tyr | Ser | Tyr | Asn | Ala | Phe | Ile |
|---|---|---|---|---|---|---|---|---|---|---|---|---|---|---|---|
|  |  |  | 100 |  |  |  |  | 105 |  |  |  |  | 110 |  |  |

| Asn | Ala | Ala | Arg | Ser | Phe | Pro | Gly | Phe | Gly | Thr | Ser | Gly | Asp | Ile | Asn |
|---|---|---|---|---|---|---|---|---|---|---|---|---|---|---|---|
|  |  | 115 |  |  |  | 120 |  |  |  |  | 125 |  |  |  |  |

```
Ala  Arg  Lys  Arg  Glu  Ile  Ala  Ala  Phe  Phe  Ala  Gln  Thr  Ser  His  Glu
     130                 135                      140

Thr  Thr  Gly  Gly  Trp  Ala  Ser  Ala  Pro  Asp  Gly  Pro  Tyr  Ala  Trp  Gly
145                      150                      155                      160

Tyr  Cys  Phe  Leu  Arg  Glu  Arg  Gly  Asn  Pro  Gly  Asp  Tyr  Cys  Pro  Pro
                    165                      170                      175

Ser  Ser  Gln  Trp  Pro  Cys  Ala  Pro  Gly  Arg  Lys  Tyr  Phe  Gly  Arg  Gly
               180                      185                      190

Pro  Ile  Gln  Ile  Ser  His  Asn  Tyr  Asn  Tyr  Gly  Pro  Cys  Gly  Arg  Ala
          195                      200                      205

Ile  Ala  Val  Asp  Leu  Leu  Asn  Asn  Pro  Asp  Leu  Val  Ala  Thr  Asp  Pro
     210                      215                      220

Val  Ile  Ser  Phe  Lys  Thr  Ala  Leu  Trp  Phe  Trp  Met  Thr  Pro  Gln  Ser
225                      230                      235                      240

Pro  Lys  Pro  Ser  Cys  His  Asp  Val  Ile  Ile  Gly  Arg  Trp  Asn  Pro  Ser
                    245                      250                      255

Ser  Ala  Asp  Arg  Ala  Ala  Asn  Arg  Leu  Pro  Gly  Phe  Gly  Val  Ile  Thr
               260                      265                      270

Asn  Ile  Ile  Asn  Gly  Gly  Leu  Glu  Cys  Gly  Arg  Gly  Thr  Asp  Asn  Arg
          275                      280                      285

Val  Gln  Asp  Arg  Ile  Gly  Phe  Tyr  Arg  Arg  Tyr  Cys  Ser  Ile  Leu  Gly
     290                      295                      300

Val  Thr  Pro  Gly  Asp  Asn  Leu  Asp  Cys  Val  Asn  Gln  Arg  Trp  Phe  Gly
305                      310                      315                      320

Asn  Ala  Leu  Leu  Val  Asp  Val  Asp  Thr  Leu
                    325                      330
```

( 2 ) INFORMATION FOR SEQ ID NO:9:

( i ) SEQUENCE CHARACTERISTICS:
        ( A ) LENGTH: 318 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:9:

```
Ile  Trp  Ser  Val  Gly  Val  Val  Trp  Met  Leu  Leu  Leu  Val  Gly  Gly  Ser
1                   5                        10                       15

Tyr  Gly  Glu  Gln  Cys  Gly  Arg  Gln  Ala  Gly  Gly  Ala  Leu  Cys  Pro  Gly
               20                       25                       30

Gly  Asn  Cys  Cys  Ser  Gln  Phe  Gly  Trp  Cys  Gly  Ser  Thr  Thr  Asp  Tyr
          35                       40                       45

Cys  Gly  Pro  Gly  Cys  Gln  Ser  Gln  Cys  Gly  Gly  Pro  Ser  Pro  Ala  Pro
     50                       55                       60

Thr  Asp  Leu  Ser  Ala  Leu  Ile  Ser  Arg  Ser  Thr  Phe  Asp  Gln  Met  Leu
65                       70                       75                       80

Lys  His  Arg  Asn  Asp  Gly  Ala  Cys  Pro  Ala  Lys  Gly  Phe  Tyr  Thr  Tyr
                    85                       90                       95

Asp  Ala  Phe  Ile  Ala  Ala  Ala  Lys  Ala  Tyr  Pro  Ser  Phe  Gly  Asn  Thr
               100                      105                      110

Gly  Asp  Thr  Ala  Thr  Arg  Lys  Arg  Glu  Ile  Ala  Ala  Phe  Leu  Gly  Gln
          115                      120                      125

Thr  Ser  His  Glu  Thr  Thr  Gly  Gly  Trp  Ala  Thr  Ala  Pro  Asp  Gly  Pro
     130                      135                      140
```

-continued

```
Tyr Ala Trp Gly Tyr Cys Phe Val Arg Glu Arg Asn Pro Ser Thr Cys
145                 150                 155                 160

Ser Ala Thr Pro Gln Phe Pro Cys Ala Pro Gly Gln Gln Tyr Tyr Gly
                165                 170                 175

Arg Gly Pro Ile Gln Ile Ser Trp Asn Tyr Asn Tyr Gly Gln Cys Gly
            180                 185                 190

Arg Ala Ile Gly Val Asp Leu Leu Asn Lys Pro Asp Leu Val Ala Thr
            195                 200                 205

Asp Ser Val Ile Ser Phe Lys Ser Ala Leu Trp Phe Trp Met Thr Ala
        210                 215                 220

Gln Ser Pro Lys Pro Ser Ser His Asp Val Ile Thr Ser Arg Trp Thr
225                 230                 235                 240

Pro Ser Ser Ala Asp Val Ala Ala Arg Arg Leu Pro Gly Tyr Gly Thr
                245                 250                 255

Val Thr Asn Ile Ile Asn Gly Gly Leu Glu Cys Gly Arg Gly Gln Asp
            260                 265                 270

Ser Arg Val Gln Asp Arg Ile Gly Phe Phe Lys Arg Tyr Cys Asp Leu
        275                 280                 285

Leu Gly Val Gly Tyr Gly Asn Asn Leu Asp Cys Tyr Ser Gln Thr Pro
        290                 295                 300

Phe Gly Asn Ser Leu Leu Leu Ser Asp Leu Val Thr Ser Gln
305                 310                 315
```

( 2 ) INFORMATION FOR SEQ ID NO:10:

( i ) SEQUENCE CHARACTERISTICS:
        ( A ) LENGTH: 43 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:10:

```
Glu Gln Cys Gly Arg Gln Ala Gly Gly Lys Leu Cys Pro Asn Asn Leu
1               5                   10                  15

Cys Cys Ser Gln Trp Gln Trp Cys Gly Ser Thr Asp Glu Tyr Cys Ser
            20                  25                  30

Pro Asp His Asn Cys Gln Ser Asn Cys Lys Asp
            35                  40
```

( 2 ) INFORMATION FOR SEQ ID NO:11:

( i ) SEQUENCE CHARACTERISTICS:
        ( A ) LENGTH: 43 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:11:

```
Gln Gln Cys Gly Arg Gln Lys Gly Gly Ala Leu Cys Ser Gly Asn Leu
1               5                   10                  15

Cys Cys Ser Gln Phe Gly Trp Cys Gly Ser Thr Pro Glu Phe Cys Ser
            20                  25                  30

Pro Ser Gln Gly Cys Gln Ser Arg Cys Thr Gly
            35                  40
```

( 2 ) INFORMATION FOR SEQ ID NO:12:

( i ) SEQUENCE CHARACTERISTICS:
    ( A ) LENGTH: 43 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:12:

```
Gln Gln Cys Gly Arg Gln Arg Gly Gly Ala Leu Cys Gly Asn Asn Leu
1               5                   10                  15
Cys Cys Ser Gln Phe Gly Trp Cys Ser Ser Thr Pro Glu Tyr Cys Ser
            20                  25                  30
Pro Ser Gln Gly Cys Gln Ser Gln Cys Thr Gly
        35                  40
```

( 2 ) INFORMATION FOR SEQ ID NO:13:

( i ) SEQUENCE CHARACTERISTICS:
    ( A ) LENGTH: 40 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:13:

```
Lys Cys Gly Ser Gln Ser Gly Gly Lys Leu Cys Pro Asn Asn Leu Cys
1               5                   10                  15
Cys Ser Gln Trp Gly Ser Cys Gly Leu Gly Ser Glu Phe Cys Gly Gly
            20                  25                  30
Gly Cys Gln Ser Gly Ala Cys Ser
        35                  40
```

( 2 ) INFORMATION FOR SEQ ID NO:14:

( i ) SEQUENCE CHARACTERISTICS:
    ( A ) LENGTH: 63 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:14:

```
Glu Gln Cys Gly Arg Gln Ala Gly Gly Ala Leu Cys Pro Gly Gly Asn
1               5                   10                  15
Cys Cys Ser Gln Phe Gly Trp Cys Gly Ser Thr Thr Asp Tyr Cys Gly
            20                  25                  30
Pro Gly Cys Gln Ser Gln Cys Gly Gly Pro Ser Pro Ala Pro Thr Asp
        35                  40                  45
Leu Ser Ala Leu Ile Ser Arg Ser Thr Phe Asp Gln Met Leu Lys
    50                  55                  60
```

( 2 ) INFORMATION FOR SEQ ID NO:15:

( i ) SEQUENCE CHARACTERISTICS:
    ( A ) LENGTH: 71 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:15:

```
Glu Gln Cys Gly Ser Gln Ala Gly Gly Ala Arg Cys Pro Ser Gly Leu
```

```
         1               5                   10                  15
Cys  Cys  Ser  Lys  Phe  Gly  Trp  Cys  Gly  Asn  Thr  Asn  Asp  Tyr  Cys  Gly
                20                      25                      30

Pro  Gly  Asn  Cys  Gln  Ser  Gln  Cys  Pro  Gly  Gly  Pro  Thr  Pro  Thr  Pro
                35                      40                      45

Pro  Thr  Pro  Pro  Gly  Gly  Gly  Asp  Leu  Gly  Ser  Ile  Ile  Ser  Ser  Ser
                50                      55                      60

Met  Phe  Asp  Gln  Met  Leu  Lys
 65                      70
```

( 2 ) INFORMATION FOR SEQ ID NO:16:

( i ) SEQUENCE CHARACTERISTICS:
        ( A ) LENGTH: 17 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:16:

```
Gln  Gly  Ile  Gly  Ser  Ile  Val  Thr  Ser  Asp  Leu  Phe  Asn  Glu  Met  Leu
 1                  5                      10                      15

Lys
```

( 2 ) INFORMATION FOR SEQ ID NO:17:

( i ) SEQUENCE CHARACTERISTICS:
        ( A ) LENGTH: 17 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:17:

```
Gln  Gly  Ile  Gly  Ser  Ile  Val  Thr  Asn  Asp  Leu  Phe  Asn  Glu  Met  Leu
 1                  5                      10                      15

Lys
```

( 2 ) INFORMATION FOR SEQ ID NO:18:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:18:

GTATGTAAAA AG                                                                    12

( 2 ) INFORMATION FOR SEQ ID NO:19:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

(i i i) HYPOTHETICAL: NO (i v) ANTI-SENSE: NO (x i) SEQUENCE DESCRIPTION: SEQ ID NO:19:

TGGGAGCAGC GG                                                                       12

(2) INFORMATION FOR SEQ ID NO:20:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:20:

TACTCTGTGT GATGA                                                                    15

(2) INFORMATION FOR SEQ ID NO:21:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:21:

TACTTGTGTG ATGA                                                                     14

(2) INFORMATION FOR SEQ ID NO:22:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:22:

AATTTTTTAA                                                                          10

(2) INFORMATION FOR SEQ ID NO:23:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (i i) MOLECULE TYPE: DNA (genomic)

(i i i) HYPOTHETICAL: NO (i v) ANTI-SENSE: NO ( x i ) SEQUENCE DESCRIPTION: SEQ ID NO:23:

TTAAAAAATT               10

( 2 ) INFORMATION FOR SEQ ID NO:24:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:24:

TCCCCAAGGT               10

( 2 ) INFORMATION FOR SEQ ID NO:25:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:25:

TGGAACCCCT               10

( 2 ) INFORMATION FOR SEQ ID NO:26:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:26:

ATGCATGCAT ATGCAT               16

PLANT DEFENSE GENES AND PLANT DEFENSE REGULATORY ELEMENTS

This application is a divisional application of U.S. Ser. No. 07/704,288, filed May 22, 1991, now U.S. Pat. No. 5,399,680, the entire contents of which is hereby incorporated by reference herein.

The present invention relates to regulatory elements functional in plants, especially monocotyledons. In addition, the present invention relates to novel plant genes encoding products involved in plant defense.

BACKGROUND OF THE INVENTION

The response of plants to microbial attack involves de novo synthesis of an array of proteins designed to restrict the growth of the pathogen. These proteins include hydroxyproline-rich glycoproteins, proteinase inhibitors, enzymes for the synthesis of phytoalexins, enzymes contributing to the reinforcement of cell walls, and certain hydrolytic enzymes such as chitinase and glucanase.

Plant defenses can also be activated by elicitors derived from microbial cell walls and culture fluids. In dicotyledonous plants, extensive studies have shown that microbial attack or elicitor treatment induces the transcription of a battery of genes encoding proteins involved in these defense responses, as part of a massive switch in the overall pattern of gene expression. The functional properties of the promoters of several of these dicotyledonous defense genes have been characterized. In contrast, relatively little is known about the inducible defenses in monocotyledonous plants, including the major cereal crops. For example, the transcriptional regulation of defense genes from monocotyledonous plants has not been examined.

Chitinase (EC 3.2.1.14) catalyzes the hydrolysis of the β-1,4 linkages of the N-acetyl-D-glucosamine polymer chitin. Chitin does not occur in higher plants, but is present in the cell walls of many fungi. Chitinase, which exhibits complex developmental and hormonal regulation, has been found in many species of higher plants. In addition, chitinase activity is markedly increased by wounding, ethylene, or microbial elicitors. Furthermore, chitinase is involved in the hypersensitive resistance response to microbial attack. Purified plant chitinase attacks and partially digests isolated cell walls of potentially pathogenic fungi. It is this latter enzyme activity, rather than chitin-binding lectin activity, that is responsible for the inhibition of fungal growth. Chitinase and β-glucanase exhibit synergistic antifungal activity in vitro. A number of pathogenesis-related proteins (also referred to as "PR proteins") have been found to be chitinases or glucanases.

Chitinase genes from a number of dicotyledonous plants (including bean, cucumber, potato, and tobacco) have been isolated and characterized.

Plant chitinases can be divided into at least three classes, based on amino acid sequence and cellular localization. Class I chitinases are basic isoforms which are structurally homologous and are primarily localized in the central vacuole. Basic chitinases contain a catalytic domain, and a cysteine-rich domain similar to rubber hevein. The hevein domain is thought to serve as an oligosaccharide-binding site. There is a variable spacer region between the hevein and the catalytic domains.

Class II chitinases are usually found in the extracellular fluid of leaves and in the culture medium of cell suspensions, suggesting that they are localized in the apoplastic compartment, consistent with a major function in defense. This hypothesis is supported by recent observations that some PR proteins are acidic chitinases.

Class III chitinases, such as a recently described cucumber chitinase, show no homology with either Class I or Class II chitinases, but are homologous to a lysozyme/chitinase from *Parthenocissus quinquifolia*. Class III chitinases are located in the extracellular compartment.

While chitinases from dicotyledons have been well characterized, and many of the corresponding genes have been isolated, there is little information available on the structure and expression of chitinase genes from monocotyledons.

SUMMARY OF THE INVENTION

In accordance with the present invention, we have isolated and characterized a monocotyledon chitinase gene and its associated regulatory sequences. The regulatory sequences of the invention are highly expressed in certain floral organs, and are highly inducible from a low basal level of expression upon exposure to plant defense elicitors.

The regulatory sequences of the invention are useful, for example, for the controlled expression of a wide variety of gene products, such as reporter constructs, functional proteins (e.g., enzymes), and the like.

BRIEF DESCRIPTION OF THE DRAWINGS

FIG. 1 presents a comparison of the amino acid sequences of the invention chitinase (derived from rice), Sequence ID No. 3, with the amino acid sequences of basic chitinases from dicotyledon plants. The predicted amino acid sequence of RCH10 is shown on the top line, while amino acid sequences of tobacco (Sequence ID No. 6), potato (Sequence ID Nos. 7–8), and bean (Sequence ID No. 9) basic chitinases are aligned with the RCH10 sequence. Only amino acids differing from the RCH10 sequence are shown. "Dots" indicate gaps in the sequence comparison; while an "*" indicates a stop codon.

FIG. 2 presents a comparison of the amino acid sequence of the RCH10 hevein domain, Sequence ID No. 3 (amino acid residues 22–92), with the amino acid sequences of the hevein domains of other proteins, i.e., rubber hevein, Sequence ID No. 10, [amino acid residues 1–43; see Lucas et al., FEBS Lett. 193: 208–210 (1985)], potato WIN1, Sequence ID No. 11, and WIN2, Sequence ID No. 12, [amino acid residues 26–68 of each; see Stanford et al., Mol. Gen. Genet. 215: 200–208 (1989)], wheat germ agglutinin isolectin, Sequence ID No. 13, [WGA, amino acid residues 88–127; see Wright et al., Biochemistry 23: 280–287 (1984)], rice RCH10, Sequence ID No. 3, (amino acid residues 22–92), bean basic chitinase, Sequence ID No. 14, [amino acid residues 1–79; see Broglie et al., Proc. Natl. Acad. Sci. USA 83: 6820–6824 (1986)], tobacco basic chitinase, Sequence ID No. 15, (amino acid residues 1–87); tobacco PR-P Sequence ID No. 17 and PR-Q Sequence ID No. 16, proteins (amino acid residues 25–57 of each) [see Payne et al., Proc. Natl. Acad. Sci. USA 87: 98–102 (1990) with respect to each of the tobacco sequences]. Each of the above sequences were aligned to maximize sequence identity; only amino acids which differ from the rubber hevein sequence are set forth in the Figure.

FIG. 3A deals with wound and elicitor induction in leaf tissue; FIG. 3B deals with developmental expression in vegetative organs; and FIG. 3C deals with developmental expression in floral organs.

FIG. 4A presents results using a substantially intact promoter (including nucleotides −1512 to +76, with respect to the transcription start site; also presented as nucleotides 374–1884 of Sequence ID No. 1, plus nucleotides 1–76 of Sequence ID No. 2; referred to as construct BZ4-1); FIG. 4B presents results with a deleted promoter (including only nucleotides −160 to +76, with respect to the transcription start site; also presented as nucleotides 1724–1884 of Sequence ID No. 1, plus nucleotides 1–76 of Sequence ID No. 2; referred to as construct BZ10-1). Open circles designate wounded leaves, while closed circles designate wounded leaves which have also been exposed to elicitor.

DETAILED DESCRIPTION OF THE INVENTION

Figure 3A:
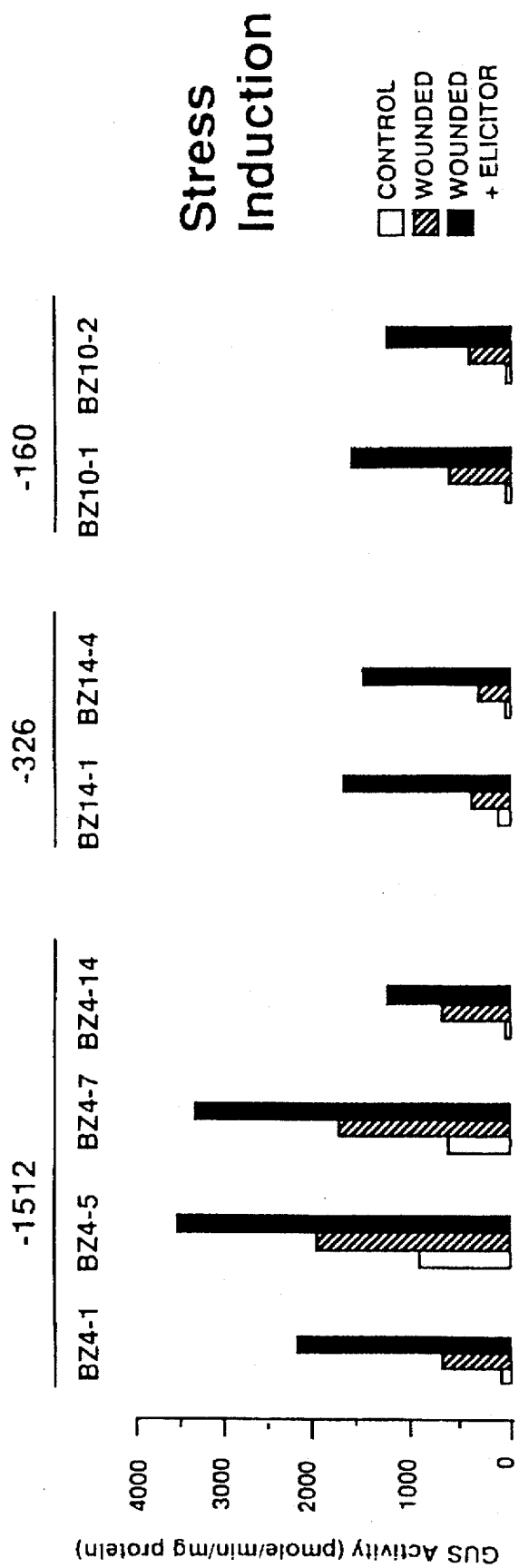
FIGS. 3A–3C collectively summarize expression results with RCH10-GUS gene fusions in transgenic tobacco plants.

In accordance with the present invention, there is provided a DNA fragment comprising a monocotyledon promoter characterized as being responsive to physical and/or biological stress; wherein said DNA fragment is further characterized by the following relative pattern of expression in mature plants:

a low level of expression in leaves;

a moderate level of expression in plant stems; and the highest level of expression in the plant roots and in the male and female parts of plant flowers.

In accordance with another embodiment of the present invention, there are provided DNA construct(s) comprising the above-described monocotyledon promoter, operatively linked to at least one structural or functional gene, e.g., a reporter gene.

In accordance with yet another embodiment of the present invention, there is provided plant material transformed with the above-described DNA construct(s).

In accordance with still another embodiment of the present invention, there is provided a method for inducing the expression of heterologous, functional gene(s) in monocotyledon and dicotyledon plants, said method comprising:

subjecting the above-described plant material to conditions which induce transcription of said DNA construct (s).

In accordance with a further embodiment of the present invention, there are provided substantially pure proteins having in the range of about 300 up to 350 amino acids, characterized by:

a hevein domain having in the range of about 40 up to 80 amino acids, wherein said hevein domain is about 70% homologous with respect to dicotyledonous chitinase hevein domains;

a glycine- and arginine-rich spacer region having in the range of about 6 up to 12 amino acids; and a catalytic domain having in the range of about 240 up to 280 amino acids, wherein said catalytic domain is about 77% homologous with respect to dicotyledenous chitinase catalytic domains.

Proteins of the present invention can optionally further comprise a signal peptide having in the range of about 16 up to 30 amino acids.

A presently preferred protein of the invention has about 336 amino acids, wherein:

the hevein domain has about 40 amino acids;

the glycine- and arginine-rich spacer region has about 12 amino acids; and the catalytic domain has about 262 amino acids.

This presently preferred peptide will optionally have a signal peptide of about 21 amino acids.

In accordance with a still further embodiment of the present invention, there are provided DNA sequences encoding the above-described protein, optionally further containing a readily detectable label.

In accordance with yet another embodiment of the present invention, there is provided a method for the identification of novel chitinase genes, said method comprising probing a nucleic acid library with at least a portion of the above-described labeled DNA under suitable hybridization conditions, and selecting those clones of said library which hybridize with said probe.

The DNA fragment comprising a monocotyledon promoter contemplated by the present invention is responsive to physical and/or biological stress. As used herein, the term "responsive to physical and/or biological stress" refers to DNA sequences which are responsive to exposure to physical stress, such as, for example, wounding (e.g., tearing, folding, bending, and the like), bruising, and the like; or to biological stress, such as, for example, plant defense elicitors (e.g., the high molecular weight fraction heat-released from the cell walls of the soybean fungal pathogen *Phytophthira megasperma* f. sp. *glycinea*, purified glucan elicitors, and the like); and so forth.

The relative expression pattern of peptides maintained under the expression control of the invention monocotyledon promoter in mature plants is typically as follows:

a low level of expression in leaves;

a moderate level of expression in plant stems; and the highest level of expression in the plant roots and in the male and female parts of plant flowers.

The monocotyledon promoter of the present invention can be further characterized by reference to the sequences set forth in the Sequence Listing provided herewith, referring specifically to Sequence ID No. 1 (and Sequence ID No. 2). For example, a DNA fragment having substantially the same sequence as nucleotides 1836 to 1884, as set forth in Sequence ID No. 1, is operative to confer responsiveness to physical and/or biological stress on a gene associated therewith. Of course, those of skill in the art recognize that longer fragments from the upstream portion of the invention chitinase gene can also be used, such as, for example, a DNA fragment having substantially the same sequence as nucleotides 1810 to about 1884, as set forth in Sequence ID No. 1; a DNA fragment having substantially the same sequence as nucleotides 1724 to about 1884, as set forth in Sequence ID No. 1; a DNA fragment having substantially the same sequence as nucleotides 1558 to about 1884, as set forth in Sequence ID No. 1; a DNA fragment having substantially the same sequence as nucleotides 372 to about 1884, as set forth in Sequence ID No. 1; a DNA fragment having substantially the same sequence as nucleotides 1 to about 1884, as set forth in Sequence ID No. 1; and the like.

In addition, sequences downstream of the transcription start site can also be included in the regulatory elements employed herein (up to about 100 or more nucleotides derived from downstream of the transcription start site can be employed). Thus, the above-described regulatory elements can be extended to comprise, for example, nucleotides 1–76 as set forth in Sequence ID No. 2, thereby forming regulatory constructs such as:

a contiguous sequence of nucleotides comprising nucleotides 1836 to 1884, as set forth in Sequence ID No. 1, plus nucleotides 1–76 as set forth in Sequence ID No. 2;

a contiguous sequence of nucleotides comprising nucleotides 1810 to 1884, as set forth in Sequence ID No. 1, plus nucleotides 1–76 as set forth in Sequence ID No. 2;

a contiguous sequence of nucleotides comprising nucleotides 1724 to 1884, as set forth in Sequence ID No. 1, plus nucleotides 1–76 as set forth in Sequence ID No. 2;

a contiguous sequence of nucleotides comprising nucleotides 1558 to 1884, as set forth in Sequence ID No. 1, plus nucleotides 1–76 as set forth in Sequence ID No. 2;

a contiguous sequence of nucleotides comprising nucleotides 372 to 1884, as set forth in Sequence ID No. 1, plus nucleotides 1–76 as set forth in Sequence ID No. 2;

a contiguous sequence of nucleotides comprising nucleotides 1 to 1884, as set forth in Sequence ID No. 1, plus nucleotides 1–76 as set forth in Sequence ID No. 2;

and the like.

The monocotyledon promoter of the present invention can be used for the controlled expression (with respect to both spatial and temporal expression) of a wide variety of gene products. For example, promoter plus reporter constructs (e.g., wherein said reporter gene is selected from chloramphenicol acetyltransferase, β-glucuronidase, β-lactamase, firefly luciferase, and the like) can be used to monitor when and where expression from the invention promoter is induced in a host plant or plant cell.

Alternatively, constructs comprising the monocotyledon promoter of the present invention, plus structural gene, can be employed for the controlled expression of numerous structural (or functional) genes, such as, for example, the *Bacillus thuringensis* toxin gene, genes encoding enzymes involved in phytoalexin biosynthesis, proteinase inhibitor genes, lytic enzyme genes, genes encoding inducers of plant disease resistance mechanisms, and the like.

Plants contemplated for use in the practice of the present invention include both monocotyledons and dicotyledons. Monocotyledons are presently preferred because the invention monocotyledon promoter is expected to be functional in nearly all monocotyledons, whereas dicotyledon promoters have frequently been non-operative when used in monocotyledon hosts. Conversely, it is expected that the invention monocotyledon promoter(s) will be functional in many dicotyledon hosts.

Exemplary monocotyledons contemplated for use in the practice of the present invention include rice, wheat, maize, sorghum, barley, oat, forage grains, as well as other grains.

Plants or plant cells containing the above constructs (introduced by standard techniques, such as, for example, by transfection) can be used to study patterns of development, for the controlled expression of various plant defense genes, for the expression of selectable marker genes (to screen for mutants or compounds that modulate stress signal transduction pathways), and the like.

In accordance with one embodiment of the present invention, the rice chitinase structural gene has also been isolated and characterized. This gene is characterized as having only coding sequence (i.e., contains no introns), and encodes the above-described polypeptide, plus signal sequence. The rice chitinase structural gene can be further characterized as having substantially the same nucleic acid sequence as nucleotides +55 through +1062, as set forth in Sequence ID No. 2.

The rice chitinase gene of the present invention encodes a novel protein, i.e., rice basic chitinase. The rice basic chitinase of the present invention can be further characterized as having substantially the same amino acid sequence as amino acids 22–357, as set forth in Sequence ID Nos. 2 and 3 (for the mature form of rice basic chitinase) or amino acids 1–357, as set forth in Sequence ID Nos. 2 and 3 (for the precursor-form of rice basic chitinase).

Optionally, the rice chitinase structural gene, or a fragment of at least 100 contiguous nucleotides thereof, can be labeled (wherein said label is selected from a radiolabeled molecule, a fluorescent molecule, a chemiluminescent molecule, an enzyme, a ligand, a toxin, a selectable marker, etc). The resulting labeled rice chitinase structural gene (or a portion thereof) can be used, for example, as a probe (e.g., as part of a method to identify additional monocotyledon or dicotyledon chitinase-like genes), and the like.

One of skill in the art can readily determine suitable hybridization conditions for screening libraries in search of additional monocotyledon or dicotyledon chitinase-like genes. For example, one would preferably use stringent hybridization conditions when screening for other monocotyledon chitinase or chitinase-like genes; while one would likely use milder hybridization conditions when screening for dicotyledon chitinase or chitinase-like genes. Stringent hybridization conditions comprise a temperature of about 42° C., a formamide concentration of about 50%, and a moderate to low salt concentration. More mild hybridiation conditions comprise a temperature below 42° C., formamide concentrations somewhat below 50%, and moderate to high salt concentrations. Exemplary mild hybridization conditions comprise a temperature of about 37° C., a formamide concentration of about 20%, and a salt concentration of about 5× standard saline citrate (SSC; 20× SSC contains 3M sodium chloride, 0.3M sodium citrate, pH 7.0). Such conditions will allow the identification of sequences which have a substantial degree of similarity with the probe sequence, without requiring perfect homology for the identification of a stable hybrid. The phrase "substantial similarity" refers to sequences which share at least 50% homology. Preferably, hybridization conditions will be selected which allow the identification of sequences having at least 70% homology with the probe, while discriminating against sequences which have a lower degree of homology with the probe.

In the invention method for inducing gene expression in monocotyledon (and dicotyledon) plants, plant material containing DNA constructs under the expression control of invention monocotyledon regulatory sequences is subjected to conditions which induce transcription of the DNA construct. Such conditions include exposing the plant or plant material to physical stress (e.g., wounding) and/or biological stress (e.g., infection, elicitor molecules derived from pathogens).

The invention will now be described in greater detail by reference to the following non-limiting examples.

EXAMPLES

Nucleotide sequences were determined by the dideoxy chain-termination [Sanger et al., PNAS 74: 5463–5467 (1977)]. Fragments for sequencing were obtained by restriction endonuclease digestion or exonuclease III deletion [Ausubel et al., *Current Protocols in Molecular Biology*, Wiley, NY (1987)].

Example I

Plant Material

Rice (*Oryza sativa* L. cv. IR36) seeds were sterilized in 70% ethanol for 2 minutes and then in a 2% solution of sodium hypochlorite for 30 minutes. Sterilized seeds were germinated and grown in MS medium (without hormones) in darkness [Murashige and Skoog, Physiol. Plant 15: 473–497 (1962)]. Two weeks after germination, leaves, roots and stems were harvested separately, then immediately frozen in liquid nitrogen and stored at −80° C. until required. Rice (cv. CR76) cell suspension cultures were grown in N6 medium [Chu et al., Scientia Sinica 5: 659–668 (1975)] and maintained in darkness. The high molecular weight fraction heat-released from mycelial cell walls of *Phytophthora megasperma* pv. *glycinea* (Pmg) was used as elicitor [Sharp et al., J. Biol. Chem. 259: 11321–11326 (1984)]. Elicitation experiments were conducted on 5-day-old cultures, the stage of the cell culture cycle during which maximum responsiveness to elicitor was observed.

Example II

DNA and RNA Isolation

Genomic DNA from rice cell suspension cultures was prepared according to the method of Ausubel et al., supra. DNA was isolated from tobacco leaves as described by Schmid et al., Plant Cell 2: 619–631 (1990). Plasmid and phage DNA were isolated by standard methods [Maniatis et al., Molecular Cloning: A laboratory manual, Cold Springs Harbor Laboratories, Cold Spring Harbor, N.Y. (1982)]. RNA from cell suspension cultures and plant tissues was prepared by the guanidinium isothiocyanate method [Chomczynski and Sacchi, Anal. Biochem. 162: 156–159 (1989)].

Example III

Isolation and Characterization of Genomic Rice Clones

A lambda-DASH library containing 15–25 kb genomic fragments from a Sau3A partial digest of rice genomic DNA was a gift from N. H. Chua. pCht12.3, a 650 bp bean basic chitinase cDNA fragment cloned in pBluescript, was used as probe [Hedrick et al., Plant Physiol. 86: 182–186 (1988)]. For library screening, filters were pre-hybridized for 2–4 hours at 42° C. in 30% formamide, 5×Denhardt's solution (1×Denhardt's solution is 0.02% bovine serum albumin, 0.02% Ficoll, and 0.02% polyvinylpyrrolidone), 5×SSC (1×SSC is 0.15M NaCl, 15 mM sodium citrate), and 100 μg of sheared salmon sperm DNA per ml. The filters were then hybridized for 24 hours at 42° C. in the same buffer with nick-translated probe DNA. Filters were washed in 2×SSC, 2% SDS at 42° C. for 30 minutes and autoradiographed at −80° C. Purified phage clones containing chitinase sequences were analyzed by restriction endonuclease digestion and Southern blot hybridization. Selected restriction fragments were subcloned into pGEM7 or pBluescript vector.

Example IV

DNA Blot Hybridization

Rice genomic DNA samples were digested with various restriction enzymes, fractionated by electrophoresis on a 1% agarose gel and blotted onto a nylon membrane (Genescreen plus). Hybridization to genomic DNA was performed for 24 hours at 65° C. in 1% SDS, 1M NaCl, 10% dextran sulfate, 100 μg per ml sheared, denatured salmon sperm DNA, and the DNA probe labeled with [$^{32}$P]. The membrane was washed with constant agitation, twice in 2×SSC for 5 minutes at room temperature and once in 2×SSC, 1% SDS for 45 minutes at 65° C.

Genomic Southern blots with tobacco DNA were probed with the HindIII/SacII fragment of pBI101 containing GUS coding sequences using standard procedures.

Example V

RNA Blot Hybridization

RNA samples were separated by electrophoresis on a 1% agarose formamide gel in 1×3-[N-morpholino]-propanesulfonic acid (MOPS)/EDTA buffer (10×MOPS/EDTA buffer is 0.5M MOPS, pH 7.0, 0.01M EDTA, pH 7.5), and blotted onto a nylon membrane. Before hybridization, the membranes were baked at 80° C. for 2 hours. The same hybridization conditions as in Southern blot analysis were used, except that hybridization was at 60° instead of 65° C.

Example VI

Fusion Protein Analysis

A 941 bp fragment from the chitinase RCH10 coding region (positions +85 to +1026 relative to the transcription start site; nucleotides 85–1026, see Sequence ID No. 2) was inserted into pRX-1, pRX-2, and pRX-3 expression vectors [Rimm and Pollard, Gene 75: 323–327 (1989)] to generate pBZ7-1, pBZ7-2, and pBZ7-3, respectively. These plasmids were transferred into *Escherichia coli* strain HB101 by the CaCl$_2$ method [Maniatis et al. supra], and the transformed cells grown to stationary phase at 37° C. in LB broth. The cells were then inoculated into 5 ml of M9-CA minimal medium containing 100 μg/ml ampicillin, grown for 3 hours at 37° C., and then induced by addition of indolylacrylic acid to a final concentration of 10 μg/ml. After 5 hours, the cells were harvested and lysed by sunication in 10 mM TRIS-HCl, pH 8.0, 50 mM EDTA, 8% sucrose, 0.5% Triton X-100, and lysozyme (2 mg/ml). Soluble bacterial extracts were analyzed in a 10% SDS-polyacrylamide gel [Maniatis et al. supra]. Immunoblotting was performed as described by Bradley et al., Planta 173: 149–160 (1988). Antiserum to bean chitinase, prepared employing standard techniques, was obtained as a gift from T. Boller.

Example VII

Isolation and Nucleotide Sequence of RCH10

A rice genomic library was screened using as a probe the insert of pCht12.3, which contains cDNA sequences of a bean basic chitinase [Hedrick et al., supra]. From 12 plaque-purified clones, 3 positive clones were characterized by restriction mapping and Southern blot hybridization. A 2.5 kb HindIII fragment from one of these clones, designated RCH10, was subcloned. Nucleotide sequencing showed that this fragment contained a 1.0 kb open reading frame (ORF), together with 1.5 kb of upstream sequence. Subcloning of two HincII fragments that overlapped the HindIII fragment gave an additional 372 bp of nucleotide sequence 5' of the HindIII fragment and 125 bp 3' of this fragment. This 3.0 kb sequence contained the complete RCH10 chitinase gene (see Sequence ID No. 1).

A single long ORF with no introns encoded a polypeptide of 336 amino acids (see FIG. 1 and Sequence ID No. 2). FIG. 1 shows the primary structure of the RCH10 gene product compared with basic chitinases from dicotyledon plants. The RCH10 polypeptide contains a hydrophobic putative signal peptide of 21 amino acids at the N-terminus, as well as hevein and catalytic domains. The hevein domain of RCH10 is about 40 amino acids long and is cysteine-rich. FIG. 2 shows a comparison of the hevein domain of RCH10 with the hevein polypeptide and other gene products containing this domain, including WIN1, WIN2, and wheat germ agglutinin isolectin. The hevein domain of RCH10 shares about 70% amino acid sequence identity with these other hevein domains. The hevein domain and catalytic domain of RCH10 are separated by a glycine- and arginine-rich spacer region. The amino acid sequence identity between the RCH10 catalytic domain and the catalytic domains of chitinases from dicotyledons is about 77%.

Example VIII

TrpE-RCH10 Fusion Protein

The level of similarity between RCH10 and basic (class I) chitinase genes from dicotyledons strongly suggests that RCH10 encodes a rice chitinase. To confirm the identity of the protein product encoded by the RCH10 gene, a fragment from the coding region (positions +85 to +1026) was inserted into the E. coli expression vectors pRX1, pRX2, and pRX3 to obtain the plasmids pBZ7-1, pBZ7-2, pBZ7-3. pBZ7-1 codes for a fusion polypeptide consisting of 18 amino acids from TrpE, 3 amino acids from the linker sequence, and 314 amino acids from the chitinase gene fused in the same reading frame. pBZ7-2 and pBZ7-3 are respectively 1 and 2 bases out of frame compared to pBZ7-1. These three plasmids were transferred into E. coli strain HB101, and soluble bacterial extracts were separated in a 10% SDS-poly-acrylamide gel and stained with Coomassie blue. The results showed an additional 37.5 kDa polypeptide in the cells transformed with pBZ7-1, whereas no additional polypeptides were detected in cells transformed with pBZ7-2 or pBZ7-3. Western blot analysis showed that the 37.5 kDa species in cells transformed with pBZ7-1 reacted with antiserum to bean chitinase, confirming that the RCH10 gene encodes a rice chitinase.

Example IX

Transcription Start Site

The transcription start site was determined by primer-extension analysis using a synthetic 28-mer oligonucleotide identical to the sequence of the antisense DNA strand at residues 132–104 downstream from the translational initiation codon, Sequence ID No. 4, (5'-CCG-AAC-TGG-CTG-CAG-AGG-CAG-TTG-G-3'). Primer extension analysis was performed by the method of Jones et al., Cell 48: 79–89 (1987), using the synthetic oligonucleotide wherein the 5' terminus was labeled with [$^{32}$P]. No band was found in the reaction with RNA isolated from control cells, whereas two bands were detected in the reaction with RNA isolated from elicitor-treated cells. The major product was 186 nucleotides in length and corresponded to the position of the first 'A' in the sequence, Sequence ID No. 5, CCCTCAATCT, which closely resembles an eukaryotic transcription initiator sequence [Smale and Baltimore, Cell 57: 103–113 (1989)]. This position was designated as +1. An additional product two nucleotides smaller than the major reverse transcript was also detected. The putative translational initiation codon was 55 bp downstream from the major transcription start site.

Example X

Flanking Sequences

Putative TATA and CAAT boxes were located 44 and 75 bp respectively upstream from the transcription start site (see Sequence ID No. 1) The DNA sequence between these two boxes was GC-rich (72%). Two inverted putative GC boxes were present at positions −55 to −60 and −66 to −70 [Kadonaga et al., Trends Biochem. Sci. 11: 20–23 (1986)]. A sequence similar to the binding site for an elicitor-inducible factor in a parsley phenylalanine ammonia-lyase promoter occurred in the inverted orientation at positions −108 to −117 [Lois et al., EMBO J. 8: 1641–1648 (1989)]. An imperfectly duplicated TGTCCACGT motif was located at positions −752 to −736. In vivo footprinting studies have demonstrated constitutive binding of a nuclear factor to this motif [Lois et al., supra). Putative cis-acting elements in the 5' flanking region of RCH10 are summarized in Table 1:

TABLE 1

Repeat sequences and putative cis-elements in the RCH10 promoter

| Class | Position* | Sequence |
|---|---|---|
| TATA box | 1836–1843 | TATATAA |
| CAT box | 1806–1810 | CCAAT |
| GC box-like motif | 1815–1819 | CGCCC (inverted) |
| | 1824–1830 | CCCGCGG (inverted) |
| Elicitor-inducible PAL** footprint | 1770–1778 | TGGCAATGC (inverted) |
| Constitutive | 1133–1139 | TGTCCAA |
| PAL footprint | 1140–1146 | TGTCCAC |
| Direct repeat 1 | 331–343 | GTATGTAAAAAG (SEQ ID NO. 18) |
| | 363–374 | GTATGTAAAAAG (SEQ ID NO. 18) |
| Direct repeat 2 | 748–759 | TGGGAGCAGCGG (SEQ ID NO. 19) |
| | 912–923 | TGGGAGCAGCGG (SEQ ID NO. 19) |
| Direct repeat 3 | 1459–1473 | TACTCTGTGTGATGA (SEQ ID NO. 20) |
| | 1494–1507 | TACT-TGTGTGATGA (SEQ ID NO. 21) |
| Inverted repeat 1 | 541–550 | AATTTTTTAA (SEQ ID NO. 22) |
| | 1229–1238 | TTAAAAAATT (SEQ ID NO. 23) |
| Inverted repeat 2 | 1257–1266 | TCCCCAAGGT (SEQ ID NO. 24) |
| | 1650–1659 | TGGAACCCCT (SEQ ID NO. 25) |
| Triplicated motif | 1723–1738 | ATGCATGCATATGCAT (SEQ ID NO. 26) |

*Numbers refer to the sequence presented in sequence ID No. 1
**PAL = phenylalanine ammonia-lyase A computer-aided search failed to identify significant sequence homology between the rice RCH10 promoter and the promoter of an ethylene-inducible bean chitinase [Broglie et al., Proc. Natl. Acad. Sci. USA 83: 6820–6824 (1989)]. Two putative polyadenylation signals at positions 1054 (AAATAA; see Sequence ID No. 2) and 1093 (AATAAA; see Sequence ID No. 2) were found in the 3' flanking region. These sequences fit the consensus polyadenylation sequence (A/GAATAA) described in plants [Heidecker and Messing, Annu. Rev. Plant Physiol. 37: 439–466 (1986)].

Example XI

Organization of Rice Chitinase Genes

To estimate the number of chitinase genes in the rice genome, Southern blots of genomic DNA from rice were hybridized with the SacII-HindIII fragment of pRCH10 (positions 422 to 1021; see Sequence ID No. 2), which encodes a region conserved among class I and class II chitinases. This probe hybridized to several restriction fragments of rice genomic DNA digested with EcoRI, ClaI, HindIII or PvuII, indicating the presence of a family of chitinase genes in the rice genome.

Example XII

Chitinase Gene Expression in Plants and Elicitor-treated Cell Populations

RNA isolated from rice cell suspension cultures treated with the Pmg fungal elicitor were hybridized with the fragment from the conserved region of the RCH10 gene, and also with an RCH10-specific sequence, the SphI-MluI fragment (positions 114 to 259; see Sequence ID No. 2). A low basal level of chitinase transcripts could be detected in cells of suspension cultures when the fragment from the conserved region was used as probe. However, when the RCH10-specific fragment was used as the probe, no basal level of transcripts was detectable. Thus, the basal level of chitinase transcripts in cells in cultured suspension was not due to RCH10, but represented the expression of other members of the gene family. Following treatment with Pmg elicitor, accumulation of chitinase transcripts could be detected within 2 hours, with maximum levels after 6 hours. Hybridization with the RCH10-specific probe showed a similar marked accumulation of the RCH10 transcript over the time course of 2–6 hours. Northern blot analysis of RNA from different organs showed that transcripts of rice chitinase accumulate to high levels in roots, but only to barely detectable levels in stems and leaves.

Example XIII

Construction of Gene Fusions

A 2538 bp HindIII fragment from the RCH10 gene was subcloned into pGEM7, and a HindIII/BalI fragment (a contiguous fragment containing nucleotides 372–1884 of Sequence ID No. 1, plus nucleotides 1–76 of Sequence ID No. 2) was then inserted into the HindIII/SmaI site of the GUS expression vector pBI101.2 [Jefferson et al., EMBO J 6: 3901–3907 (1987)] to give pBZ4. A 1463 bp HincII fragment from RCH10 was cloned into the pGEM7 SmaI site, and a XbaI/BalI fragment (a contiguous fragment containing nucleotides 1558–1884 of Sequence ID No. 1, plus nucleotides 1–76 of Sequence ID No. 2) was then inserted into the XbaI/SmaI site of pBI101.2 to give pBZ14. A 276 bp SphI fragment from RCH10 was cloned into pSP72, and a HindIII/BalI fragment (a contiguous fragment containing nucleotides 1724–1884 of Sequence ID No. 1, plus nucleotides 1–76 of Sequence ID No. 2) was then inserted into the HindIII/SmaI site of pBI101.2 to give pBZ10. The RCH10-GUS translational fusions in pBZ4, pBZ14 and pBZ10 were confirmed by direct double-stranded sequencing using a GUS-specific primer.

Example XIV

Tobacco Transformation pBZ4, pBZ14 and pBZ10 were mobilized from *Escherichia coli* HB101 into *Agrobacterium tumefaciens* LBA 4404 [Jefferson et al., supra], and transgenic tobacco plants generated by the leaf disc method [Rogers et al., Methods Enzym. 118:627–640 (1986)]. Transformed plants were selected on Murashige and Skoog medium [Murashige and Skoog, supra] containing 200 µg/ml kanamycin and 500 µg/ml carbenicillin or cefatoxim, and grown at 25° C. under a 16-hour light (115 mE)/8-hour dark cycle.

Example XV

Wound and Elicitor Induction

Discs (about 8 mm in diameter) excised from fully expanded leaves were incubated in 50 mM sodium phosphate buffer (pH 7.0) at 25° C. in the dark. Tissue samples were snap frozen in liquid nitrogen and stored at −80° C. Fungal elicitor was the high molecular weight fraction heat-released from washed mycelial walls of *Phytophthora megasperma* f.sp. *glycinea* [Ayers et al., Plant Physiol. 57: 760–765 (1976)], and was applied to wounded tissue in 50 mM sodium phosphate buffer (pH 7.0) at a final concentration of 100 µg glucose equivalents/ml.

Excision wounding of leaf tissue caused a marked increase in GUS activity. In transformants BZ4-1 and BZ4-14, wounding resulted in 10- to 20-fold increases in GUS activity (relative to the low basal levels of 49 and 22 pmole of product/minute/mg protein, respectively, in unwounded tissue; see FIG. 3A). In transformants BZ4-5 and BZ4-7, the levels of GUS activity in unwounded leaves were 920 and 570 pmole/minute/mg protein, and wounding caused a 2- to 3-fold increase in these relatively high basal levels.

Figure 4A:
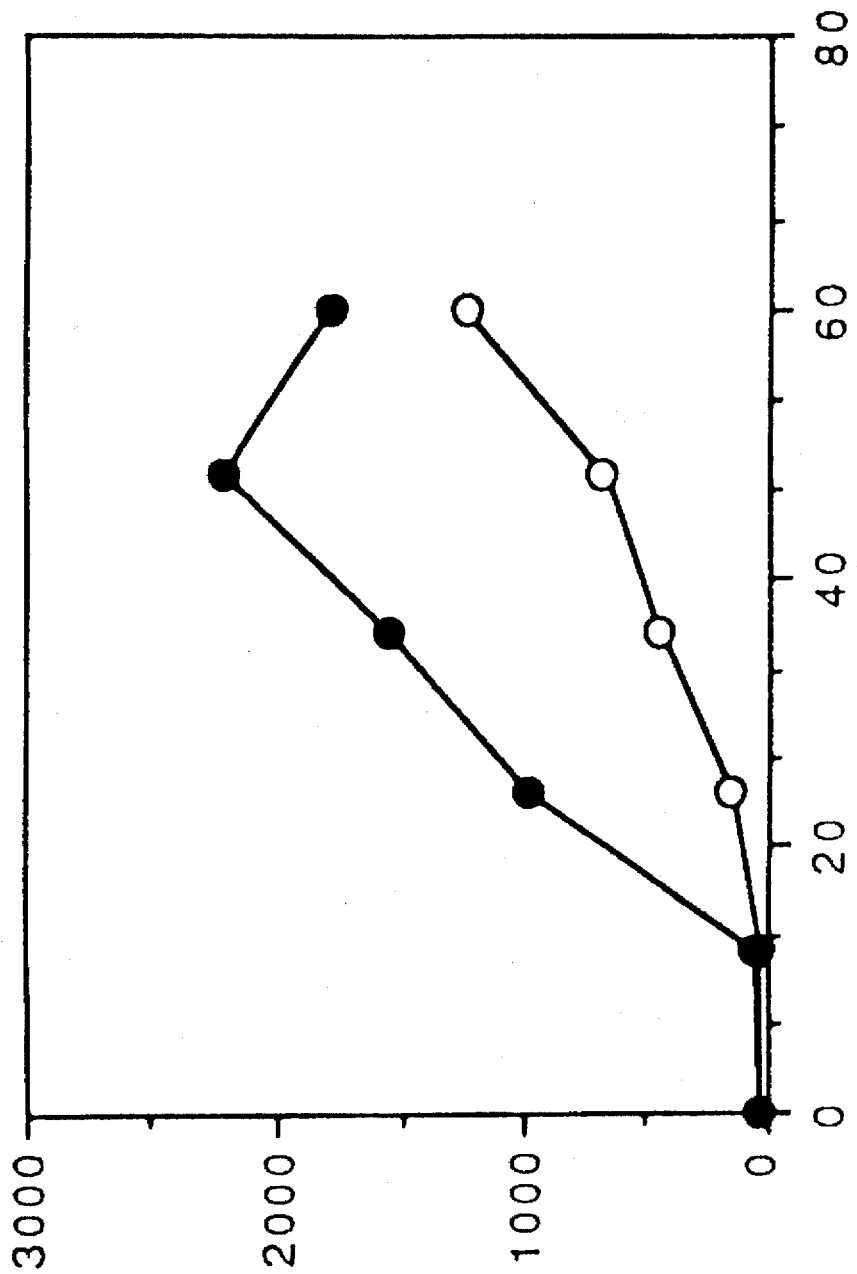
FIGS. 4A and 4B collectively present the kinetics of wound and elicitor induction of RCH10-GUS gene fusions in transgenic tobacco leaves.
Figure 4B:
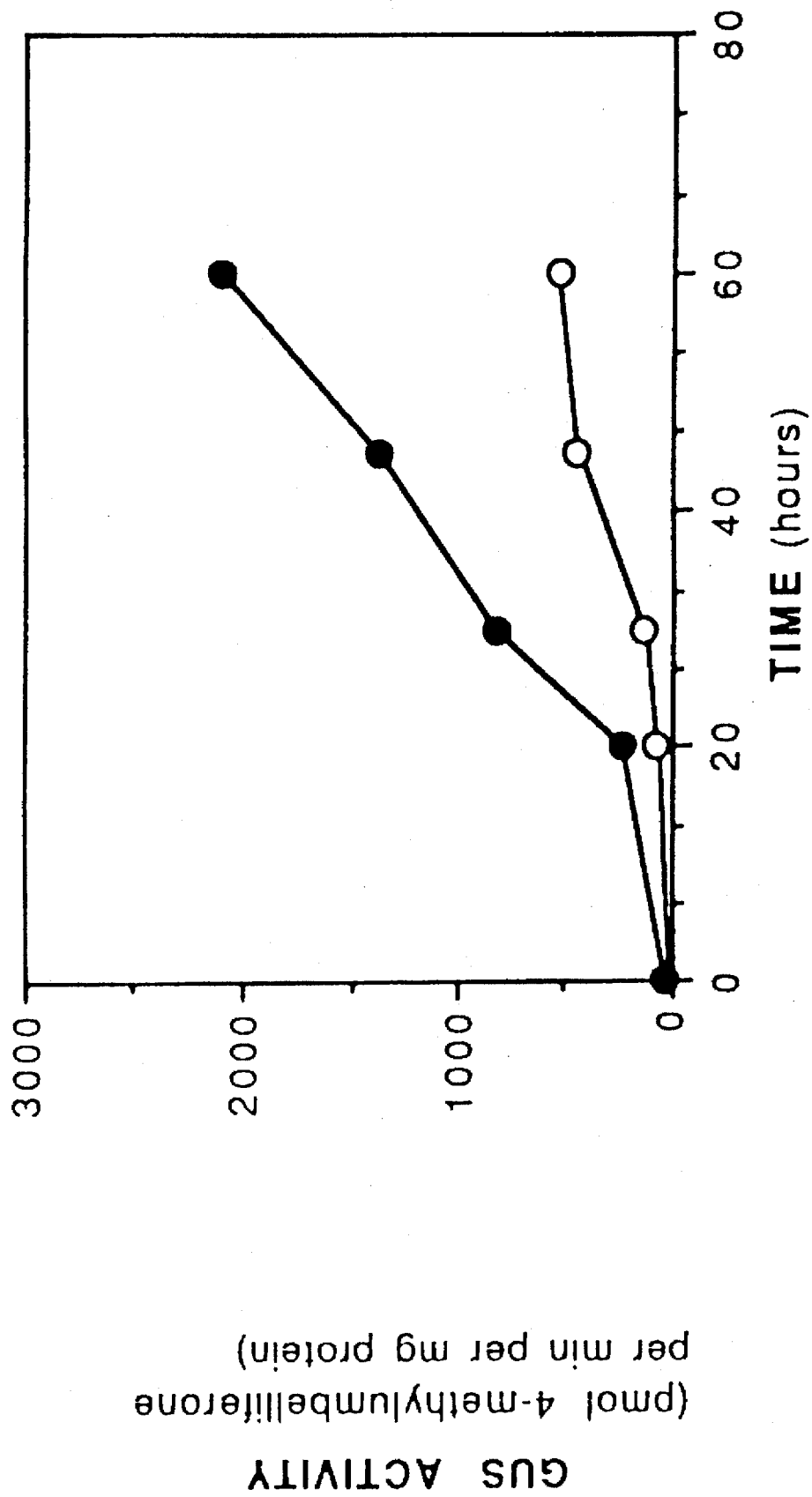

Addition of fungal elicitor to the leaf tissue immediately after excision caused a further marked stimulation of the expression of the gene fusion, compared with equivalent excision-wounded tissue not treated with elicitor (see FIG. 4A). Increased GUS activity was observed 16 hours after elicitor treatment with maximum levels after 48 hours (see FIG. 4A), whereas the response to excision wounding in the absence of elicitor was somewhat slower. Overall, elicitor treatment of excised leaf discs caused a 40- to 60-fold increase in GUS activity over low basal levels in BZ4-1 and BZ4-14 plants, compared with a 4- to 6-fold increase in BZ4-5 and BZ4-7 plants, which exhibited higher basal levels of expression (see FIG. 3A).

Histochemical analysis of GUS activity in situ showed that wound induction of the gene fusion was restricted to the tissues immediately adjacent to the wound surface, whereas elicitor also induced expression in tissues at a somewhat greater distance from the wound surface. Ethylene, administered as ethephon, had no effect on the level of GUS activity in intact leaves.

Example XVI

Developmental Expression

Figure 3B:
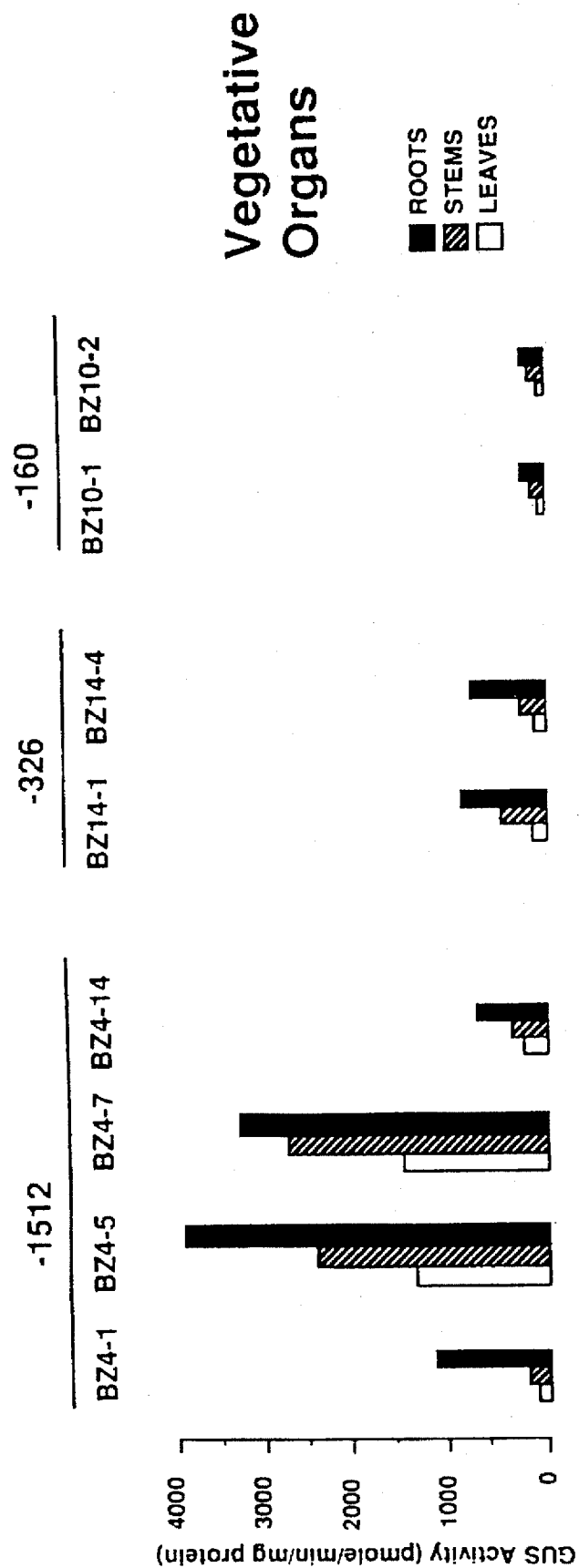

In addition to elicitor and wound induction in leaf tissue, the RCH10-GUS gene fusion was also expressed during normal development in the absence of an applied stress. Thus, high levels of GUS were observed in roots and moderate levels in stems compared to the relatively weak expression in young leaves (see FIG. 3B). Although there was, as expected, some variation among the independent transformants in the absolute levels of expression, the same overall pattern of GUS activity was observed in each case: root>stem>leaf. Histochemical analysis showed strong expression of RCH10-GUS in juvenile tissue of apical root tips. In stems, GUS staining was localized to the epidermis and vascular system. In the latter, staining was not restricted to specific tissue-types, but was observed in a number of locations including the outer phloem, inner phloem and xylem. No GUS staining was observed in pith or cortical tissue.

Figure 3C:
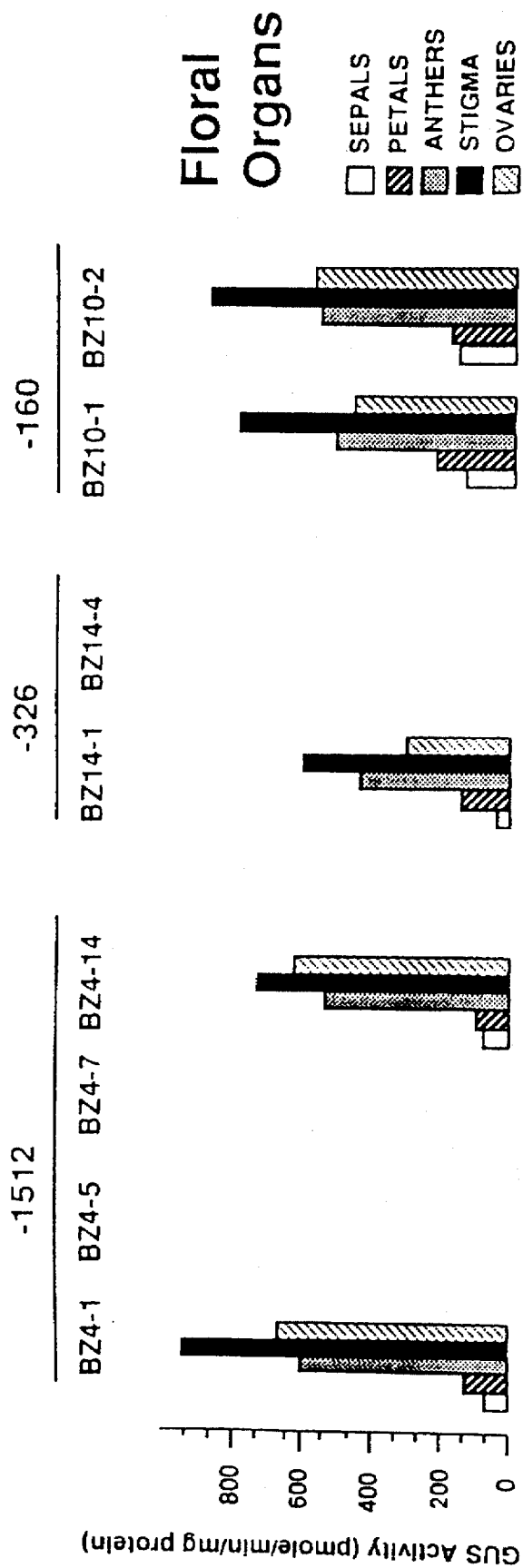

The RCH10-GUS gene fusion also exhibited a characteristic pattern of expression in floral organs. Thus while only low levels of GUS activity were observed in sepals and petals, comparable to the levels in leaves from the same plants, relatively high levels were found in anther, stigma and ovary extracts (see FIG. 3C). This organ-specific pattern of expression was confirmed by histochemical analysis of GUS activity in situ. Moreover, the in situ analysis showed that within anthers there was strong expression of the gene fusion specifically in pollen, since no staining was observed with ruptured anthers from which the pollen had been expelled, whereas strong staining was readily detectable with intact anthers containing mature pollen. GUS activity was also directly demonstrated by histochemical staining of isolated pollen.

Example XVII

Promoter Deletions

To localize cis-elements that specify the complex developmental regulation and stress induction of the RCH10 promoter, the expression was analyzed for gene fusions with upstream (i.e., 5') portions of the promoter deleted, e.g., deleted to position 1558 (see Sequence ID No. 1; BZ14) and deleted to position 1724 (see Sequence ID No. BZ10). Ten independent BZ14 transformants and 7 BZ10 transformants were examined, and in both cases two representative plants were analyzed in further detail. Strikingly, the full pattern of expression established for the BZ4 plants containing the promoter to deleted only to nucleotide 372 (see Sequence ID No. 1) was also observed in plants containing the much more extensive deletions, i.e., BZ14 (deleted to position 1558, refer to Sequence ID No. 1) or BZ10 (deleted to position 1724, refer to Sequence ID No. 1) See FIG. 3B. Thus, the BZ14 and BZ10 transformants exhibited wounding and elicitor induction of GUS activity from low basal levels in leaf tissue, with similar fold-inductions over basal levels and similar absolute levels of GUS activity in induced tissue as observed in BZ4 plants containing the full promoter (containing nucleotides 372 to 1884 as presented in Sequence ID No. 1). Likewise, the kinetics for wounding and elicitor induction of the constructs containing substantial promoter deletions (i.e., the 1558–1884 and 1724–1884 constructs) were the same as with the full promoter. The BZ14 and BZ10 plants also showed the same characteristic pattern of expression in floral organs as observed with the full promoter, with high levels of GUS activity in anthers, stigmas and ovaries compared to relatively weak expression in sepals and petals (see FIG. 3C). In vegetative organs of BZ14 and BZ10 transformants, the levels of GUS activity were: root>stem>leaf, as observed with the full promoter, although the expression in roots and stems was markedly reduced compared to BZ4 plants (see FIG. 3B).

Example XVIII

GUS Assays

GUS activity was assayed in tissue extracts by fluorimetric determination of the production of 4-methylumbelliferone from the corresponding β-glucuronide [Jefferson et al. supra; Jefferson, Plant Mol. Biol. Rep. 5: 387–405 (1987)]. Root, stem and leaf tissues were collected from 10 cm-tall plantlets and floral organs were collected from mature fully open flowers. Protein was determined by the method of Bradford [Anal. Biochem. 72: 248–254 (1976) and GUS activity was expressed as pmole of product/minute/mg of protein. Histochemical localization of GUS activity in situ was performed with the chromogenic substrate 5-bromo-4-chloro-3-indolyl β-D-glucuronide (X-gluc). Stem sections were cut by hand, vacuum-infiltrated with 50 mM sodium phosphate buffer (pH 7.0) containing X-gluc and incubated at 37° C. Flowers and roots were directly incubated in X-gluc solution. After overnight incubation, chlorophyll was removed by immersion of the tissue samples in 70% ethanol prior to examination using a Nikon Diaphot TMD microscope.

While the invention has been described in detail with reference to certain preferred embodiments thereof, it will be understood that modifications and variations are within the spirit and scope of that which is described and claimed.

SUMMARY OF SEQUENCES

Sequence ID No. 1 is the nucleic acid sequence for a regulatory region (i.e., the upstream or 5'region) of a rice chitinase gene of the invention.

Sequence ID No. 2 is the nucleic acid sequence and deduced amino acid sequence for a rice chitinase gene according to the present invention.

Sequence ID No. 3 is the deduced amino acid sequence for the rice chitinase gene presented in Sequence ID No. 2.

Sequence ID No. 4 is the nucleic acid sequence of a 28-mer oligonucleotide used in primer-extension analysis to identify the transcription start site.

Sequence ID No. 5 is a partial nucleic acid sequence of the transcription start site.

Sequence ID No. 6 is the predicted amino acid sequence of tobacco basic chitinase.

Sequence ID Nos. 7–8 are predicted amino acid sequences of potato basic chitinases.

Sequence ID No. 9 is the predicted amino acid sequence of bean basic chitinase.

Sequence ID No. 10 is the amino acid sequence of rubber hevein domain.

Sequence ID Nos. 11–12 are the amino acid sequences of potato WIN1 and WIN2 hevein domains, respectively.

Sequence ID No. 13 is the amino acid sequence of wheat germ agglutinin isolectin, WGA, hevein domain.

Sequence ID No. 14 is the amino acid sequence of bean basic chitinase hevein domain.

Sequence ID No. 15 is the amino acid sequence of tobacco basic chitinase hevein domain.

Sequence ID No. 16 is the amino acid sequence of tobacco PR-Q hevein domain.

Sequence ID No. 17 is the amino acid sequence of tobacco PR-P hevein domain.

Sequence ID Nos. 18–21 are nucleic acid sequences of direct repeat sequences in the RCH10 promoter.

Sequence ID Nos. 22–25 are nucleic acid sequences of inverted repeat sequences in the RCH10 promoter.

Sequence ID No. 26 is the nucleic acid sequence of a triplicated sequence motif in the RCH10 promoter.

That which is claimed is:

1. An isolated DNA encoding a chitinase protein wherein said DNA is selected from:
   (a) DNA encoding the amino acid sequence set forth in SEQ ID NO: 3;
   (b) naturally occurring DNA obtained from rice that hybridizes to the DNA of (a) under mild hybridization conditions, wherein said DNA encodes biologically active chitinase; or
   (c) DNA degenerate with respect to either (a) or (b) above, wherein said DNA encodes biologically active chitinase.

2. A DNA according to claim 1, wherein said DNA comprises the nucleotide sequence set forth as nucleotides 55–1062 of SEQ ID NO: 2.

3. An isolated DNA encoding a chitinase protein, wherein said DNA encodes the amino acid sequence set forth in SEQ ID NO: 3.

4. A DNA according to claim 3, or fragment thereof, wherein said DNA, or fragment thereof, further comprises a readily detectable label.

5. A DNA according to claim 4 wherein said fragment is at least about 15 nucleotides in length.

6. A DNA according to claim 4 wherein said label is a radiolabeled molecule, a fluorescent molecule, a chemiluminescent molecule, an enzyme, a ligand, a toxin, or a selectable marker.

7. A method for the identification of novel chitinase genes, said method comprising probing a nucleic acid library with at least a fragment of DNA according to claim 4 under hybridization conditions, and selecting those clones of said library which hybridize with said probe.

* * * * *